(12) United States Patent
Overstreet et al.

(10) Patent No.: US 9,220,811 B2
(45) Date of Patent: Dec. 29, 2015

(54) IMPLANTABLE OR INSERTABLE MEDICAL DEVICES

(75) Inventors: Edward Holman Overstreet, Valencia, CA (US); Anne M. Pianca, Santa Monica, CA (US); Janusz A. Kuzman, Bayview (AU); Aditya Pandit, Valencia, CA (US); Shaina Brito, Winchester, MA (US); Robert E. Richard, Wrentham, MA (US); Kerri DiPietro, Worcester, MA (US); Frederick H. Strickler, Natick, MA (US); Mark Boden, Harrisville, RI (US); Lan Pham, Nashua, NH (US); William Orinski, Stevenson Ranch, CA (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 1482 days.

(21) Appl. No.: 12/563,641

(22) Filed: Sep. 21, 2009

(65) Prior Publication Data

US 2010/0256720 A1 Oct. 7, 2010

Related U.S. Application Data

(60) Provisional application No. 61/099,139, filed on Sep. 22, 2008.

(51) Int. Cl.
*A61L 27/18* (2006.01)
*A61L 27/34* (2006.01)
(Continued)

(52) U.S. Cl.
CPC ............ *A61L 27/54* (2013.01); *A61L 27/18* (2013.01); *A61L 27/34* (2013.01); *A61N 1/0534* (2013.01); *A61N 1/0541* (2013.01); *A61N 1/0551* (2013.01); *A61L 2300/222* (2013.01); *A61L 2300/602* (2013.01)

(58) Field of Classification Search
CPC .......... A61L 27/18; A61L 27/34; C08L 83/06
USPC ........................................... 424/423; 607/117
See application file for complete search history.

(56) References Cited

U.S. PATENT DOCUMENTS

| | | | |
|---|---|---|---|
| 4,506,680 | A | 3/1985 | Stokes |
| 5,092,332 | A | 3/1992 | Lee et al. |

(Continued)

FOREIGN PATENT DOCUMENTS

| | | |
|---|---|---|
| EP | 0747069 | 11/1996 |
| WO | WO00/57948 | 5/2000 |

(Continued)

OTHER PUBLICATIONS

Sipos et al, "Controlled Delivery of Paclitaxel from Stent Coatings Using Poly(hydroxystyrene-b-isobutylene-b-hydroxystyrene) and Its Acetylated Derivative," Biomacromolecules 2005, 6, pp. 2570-2582.*

(Continued)

*Primary Examiner* — Rachael E Bredefeld
(74) *Attorney, Agent, or Firm* — Kacvinsky Daisak Bluni PLLC

(57) ABSTRACT

In various aspects, the present invention is directed to implantable neurostimulation leads and methods for their formation. In various additional aspects, the present invention is directed to medical devices having silicone-containing regions with overlying polymeric layers and to methods of forming the same.

25 Claims, 7 Drawing Sheets

(51) Int. Cl.
*A61L 27/54* (2006.01)
*C08G 77/20* (2006.01)
*A61N 1/05* (2006.01)

(56) References Cited

U.S. PATENT DOCUMENTS

| | | | |
|---|---|---|---|
| 5,103,837 A | 4/1992 | Weidlich et al. | |
| 5,178,957 A | 1/1993 | Kolpe et al. | |
| 5,200,543 A | 4/1993 | Inomata et al. | |
| 5,496,360 A | 3/1996 | Hoffmann et al. | |
| 5,609,629 A | 3/1997 | Fearnot et al. | |
| 5,630,844 A * | 5/1997 | Dogan et al. | 623/8 |
| 5,736,251 A | 4/1998 | Pinchuk | |
| 5,741,331 A | 4/1998 | Pinchuk | |
| 5,824,049 A | 10/1998 | Ragheb et al. | |
| 5,861,023 A | 1/1999 | Vachon | |
| 5,987,746 A | 11/1999 | Williams | |
| 6,101,946 A | 8/2000 | Martinsky | |
| 6,197,240 B1 | 3/2001 | Pinchuk | |
| 6,205,361 B1 | 3/2001 | Kuzma | |
| 6,259,951 B1 | 7/2001 | Kuzma et al. | |
| 6,304,786 B1 | 10/2001 | Heil, Jr. et al. | |
| 6,304,787 B1 | 10/2001 | Kuzma | |
| 6,309,410 B1 | 10/2001 | Kuzma et al. | |
| 6,395,326 B1 | 5/2002 | Castro et al. | |
| 6,545,097 B2 | 4/2003 | Pinchuk | |
| 6,584,363 B2 | 6/2003 | Heil, Jr. et al. | |
| 6,596,401 B1 | 7/2003 | Terry | |
| 6,757,970 B1 | 7/2004 | Kuzma et al. | |
| 6,862,805 B1 | 3/2005 | Kuzma et al. | |
| 6,879,695 B2 | 4/2005 | Maltan et al. | |
| 6,879,861 B2 | 4/2005 | Benz et al. | |
| 7,101,956 B2 | 9/2006 | Benz et al. | |
| 7,187,981 B2 | 3/2007 | Tanaka | |
| 7,192,450 B2 | 3/2007 | Brauker et al. | |
| 7,218,971 B2 | 5/2007 | Heil, Jr. et al. | |
| 7,282,213 B2 | 10/2007 | Schroeder et al. | |
| 7,294,345 B2 | 11/2007 | Haapakumpu et al. | |
| 7,347,751 B2 | 3/2008 | Sweeney et al. | |
| 7,363,091 B1 | 4/2008 | Chen et al. | |
| 7,410,498 B2 | 8/2008 | Penhasi | |
| 2002/0045926 A1 | 4/2002 | Heil, Jr. et al. | |
| 2002/0107330 A1 | 8/2002 | Pinchuk et al. | |
| 2002/0128419 A1 | 9/2002 | Terry et al. | |
| 2002/0198601 A1 | 12/2002 | Bales | |
| 2003/0108659 A1 | 6/2003 | Bales | |
| 2003/0171496 A1 | 9/2003 | Pinchuk et al. | |
| 2003/0235602 A1 | 12/2003 | Schwarz | |
| 2004/0078057 A1 | 4/2004 | Gibson | |
| 2004/0215306 A1 | 10/2004 | Heil, Jr. et al. | |
| 2004/0236399 A1 | 11/2004 | Sundar | |
| 2005/0027283 A1 * | 2/2005 | Richard et al. | 604/890.1 |
| 2005/0192647 A1 | 9/2005 | Hunter et al. | |
| 2005/0251225 A1 | 11/2005 | Faltys et al. | |
| 2006/0020314 A1 | 1/2006 | Bodner | |
| 2006/0111626 A1 | 5/2006 | Rossing et al. | |
| 2006/0171981 A1 | 8/2006 | Richard et al. | |
| 2006/0235499 A1 | 10/2006 | Heil, Jr. et al. | |
| 2006/0282123 A1 | 12/2006 | Hunter et al. | |
| 2006/0287689 A1 | 12/2006 | Debruyne et al. | |
| 2007/0010632 A1 | 1/2007 | Kaplan et al. | |
| 2007/0051531 A1 | 3/2007 | Borgaonkar et al. | |
| 2007/0071879 A1 | 3/2007 | Rypacek et al. | |
| 2007/0128242 A1 | 6/2007 | Zhao | |
| 2007/0168004 A1 | 7/2007 | Walter | |
| 2007/0168007 A1 | 7/2007 | Kuzma | |
| 2007/0198063 A1 | 8/2007 | Hunter et al. | |
| 2007/0213799 A1 | 9/2007 | Jolly et al. | |
| 2007/0219608 A1 | 9/2007 | Swoyer et al. | |
| 2007/0224239 A1 | 9/2007 | Behan | |
| 2007/0239245 A1 | 10/2007 | Borgaonkar et al. | |
| 2007/0250159 A1 | 10/2007 | Davis | |
| 2007/0255378 A1 | 11/2007 | Polkinghorne et al. | |
| 2007/0269485 A1 | 11/2007 | Richard et al. | |
| 2007/0280983 A1 | 12/2007 | Strickler et al. | |
| 2008/0014244 A1 | 1/2008 | Gale et al. | |
| 2008/0033520 A1 | 2/2008 | Jolly | |
| 2008/0075753 A1 | 3/2008 | Chappa | |
| 2008/0113083 A1 | 5/2008 | Sutermeister | |
| 2009/0054961 A1 | 2/2009 | Borgaonkar et al. | |
| 2009/0062896 A1 | 3/2009 | Overstreet et al. | |

FOREIGN PATENT DOCUMENTS

| | | |
|---|---|---|
| WO | WO02/41666 | 5/2002 |
| WO | WO02/43623 | 6/2002 |
| WO | WO3/034960 | 10/2002 |
| WO | WO2005/011766 | 2/2005 |
| WO | WO2005/053767 | 6/2005 |
| WO | WO2006/113335 | 10/2006 |
| WO | WO2007/030722 | 3/2007 |
| WO | WO2007/130900 | 11/2007 |
| WO | WO2007126806 | 11/2007 |
| WO | WO2007/148231 | 12/2007 |
| WO | WO2008/000045 | 1/2008 |
| WO | WO2008/014234 | 1/2008 |
| WO | WO2008/024149 | 2/2008 |
| WO | WO2008/024511 | 2/2008 |

OTHER PUBLICATIONS

U.S. Appl. No. 12/563,733, filed Sep. 21, 2009, Desai et al., Unpublished.

Aziz et al., Surface modification of an experimental silicone rubber maxillofacial material to improve wettability. Journal of Dentistry 2003 31:213-216.

Cho et al. "Synthesis, Characterization, Properties, and Drug Release of Poly(alkyl methacrylate-b-isobutylene-b-alkyl methacrylate)" *Biomacromolecules*, 7 (2006) 2997-3007.

De et al. "Carbocationic Polymerization of Isobutylene Using Methylaluminum Bromide Coinitiators: Synthesis of Bromoallyl Functional Polyisobutylene" *Macromolecules* 2006 39, 7527-7533.

Dinh et al. "Dexamethasone Protects Aginst TNF-Alpha Induced Loss of Auditory Hair Cells in Organ of Corti Explants by Altering the Expression Levels of Apoptosis-Associated Genes," Feb. 17, 2008, 1 page.

Eshraghi et al. "Local Dexamethasone Therapy Conserves Hearing in an Animal Model of Electrode Insertion Trauma-Induced Hearing Loss" *Otology & Neurotology* 2007 28:842-849.

Eshraghi et al., "Scala tympani Infusion with Dexamethasone Base (DXMb) in Artificial Perilymph Protects Against Electrode Trauma-Induced Hearting" Feb. 17, 2008, 1 page.

EUBioEar, 4 pp., downloaded on Aug. 3, 2007 http://www.uta.fi/projektit/eubioear/description.htm.

Follett et al., "Prevention and Management of Intrathecal Drug Delivery and Spinal Cord Stimulation System Infections" *Anesthesiology* 2004, 100:1582-94.

Furze et al., "Dexamethasone and methylprednisolone do not inhibit neuritic outgrowth while inhibiting outgrowth of fibroblasts from spiral ganglion explants" *Acta Oto-Laryngologica* 2008 128(2), 122-127.

Haake et al., "Bioreleased Dexamethasone Can Prevent TNF-Alpha Induced Apoptosis of Auditory Hair Cells," Feb. 17, 2008, 1 page.

Higashihara et al., "Grafting of Poly(dimethylsiloxane) onto poly-(styrene-block-isobutylene-block styrene)" *Polymer Preprints*, 2007 48(2), 1037.

Huang, et al. "Effects of steroids and lubricants on electrical impedance and tissue response following cochlear implantation" *Cochlear Implants Int.* 2007 8(3), 123-147.

Itsuno et al., "Novel Method for Halomethylation of Cross-Linked Polystyrenes" *J. Am. Chem. Soc.* 1990, 112, 8187-88.

James, et al. "Effects of Round Window Dexamethasone on Residual Hearing in a Guinea Pig Model of Cochlear Implantation" *Audiology & Neurotology* 2008;13:86-96.

Kha et al., "Determination of frictional conditions between electrode array and endosteum lining for use in cochlear implants models" *Journal of Biomechanics* 39 (2006) 1752-1756.

Laszig et al., "Intracochlear insertion of electrodes using hyaluronic acid in cochlear implant surgery" *Head and Neck Surgery* Oct. 15, 2001.

(56) References Cited

OTHER PUBLICATIONS

Plontke, et al. "Dexamethasone Concentration Gradients Along Scala Tympani After Application to the Round Window Membrane" *Otology & Neurotology 2007* 29:401-406.

Randade et al., "Styrenic block copolymers for biomaterial and drug delivery applications" *Acta Biomaterialia* 1(2005) 137-144.

Richard et al., "Evaluation of Acrylate-Based Block Copolymers Prepared by Atom Transfer Radical Polymerization as Matrices for Paclitaxel Delivery from Coronary Stents" *Biomacromolecules*, 6 (2005) 3410-3418.

Sipos et al. "Controlled Delivery of Paclitaxel from Stent Coatings Using Poly(hydroxystyrene-b-isobutylene-b-hydroxystyrene) and Its Acetylated Derivative" *Biomacromolecules* 6 (2005) 2570-2582.

Subproject D2—Nerve-Electrode Interface 2 pages, downloaded Aug. 17, 2009 from http://www.mhh-hno.de/sfb599/teilprojekte/D2/d2_en.htm.

Van De Water et al., "Is a Drug Eluting Cochlear Implant Feasible and if So What Is a Good Candidate Drug for the Conservation of Hearing?" 10$^{th}$ International Conference on Cochlear Impants and other Implantable Auditory Technologies, http://www.cic2008.com/pdfs/program_book.pdf p. 51, presentation 26, 10-12, 2008.

Virmani et al., "Localized Hypersensitivity and Late Coronary Thrombosis Secondary to a Sirolimus-Eluting Stent Should We Be Cautious?" *Circulation 2004* 109(6): 701-705.

Vivero et al. "Dexamethasone Preserves Hearing during Cochlear Implantation" Otolaryngology—Head and Neck Surgery, vol. 137, No. 2S, Aug. 2007, p. 190-p. 191.

Vivero, "Dexamethasone Base Conserves Hearing from Electrode Trauma-Induced Hearing Loss" *The Laryngoscope* 118: xx 2008, pp. 1-8.

Yuan et al. "Grafting sulfobetaine monomer onto silicone surface to improve haemocompatibility," *Polymer International* 2003 53(1), 121-126.

Zhou et al., "Syntheses and Characterization of Poly(cyclohexyl vinyl ether-stat-vinyl alcohol)-b-polyisobutylene-b-poly(cyclohexyl vinyl ether-stat-vinyl alcohol) Triblock Copolymers and Their Application as Coatings to Deliver Paclitaxel from Coronary Stents" Macromolecules, 38 (2005) 8183-8191.

\* cited by examiner

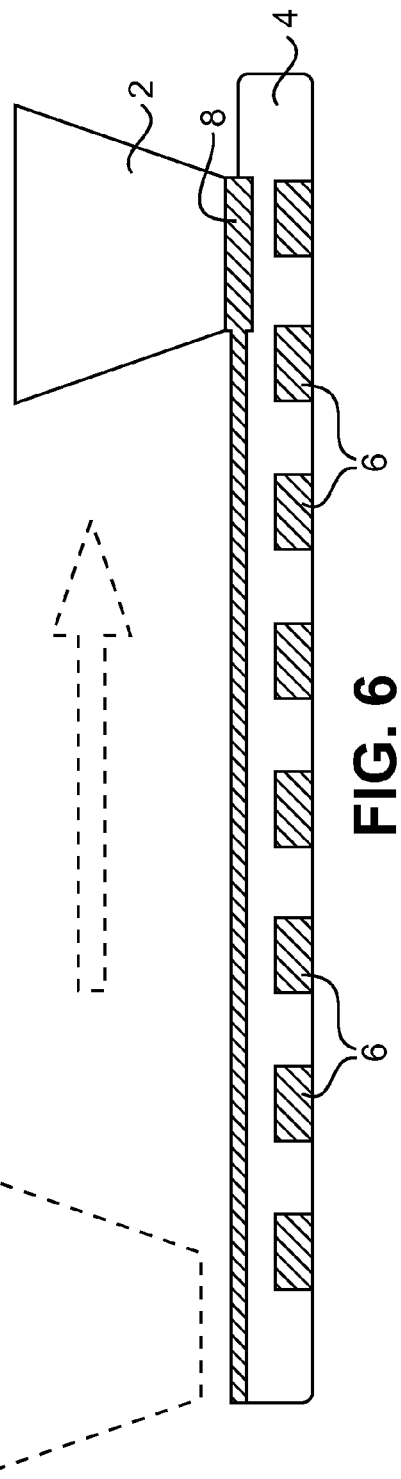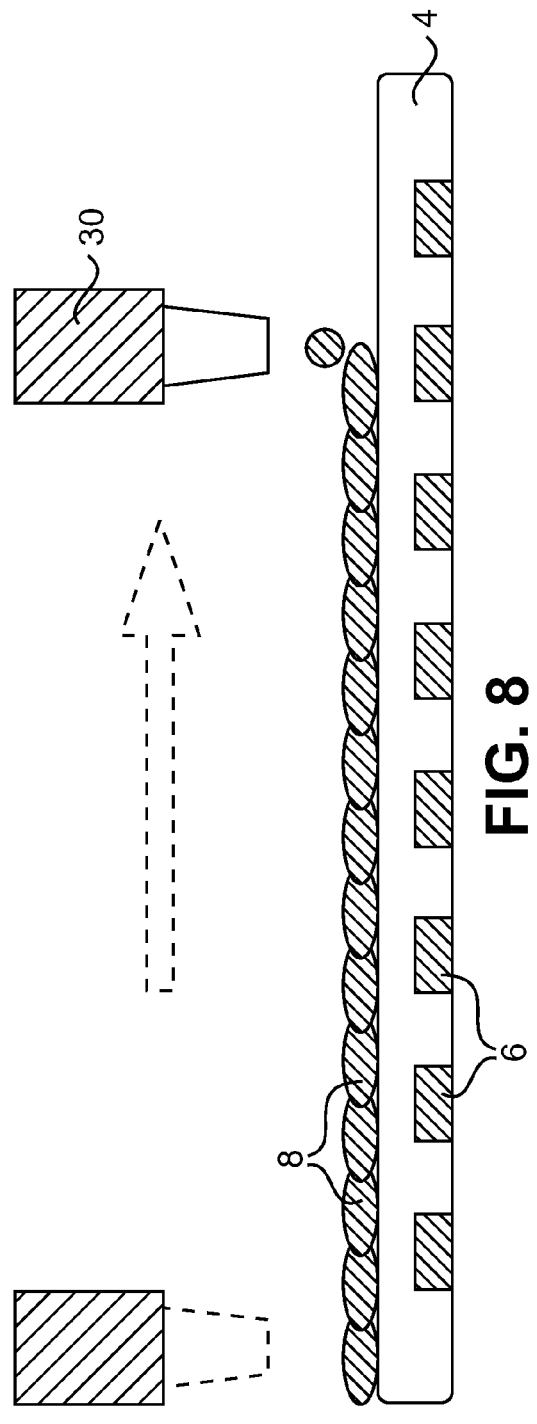

IMPLANTABLE OR INSERTABLE MEDICAL DEVICES

RELATED APPLICATION

This patent application claims the benefit of U.S. provisional application 61/099,139, filed Sep. 22, 2008, which is incorporated by reference herein in its entirety.

BACKGROUND OF THE INVENTION

Numerous polymer-based medical devices have been developed for implantation or insertion into the body. For example, in recent years, drug eluting coronary stents, which are commercially available from Boston Scientific Corp. (TAXUS and PROMUS), Johnson & Johnson (CYPHER) and others, have been employed for maintaining vessel patency. These existing products are based on metallic expandable stents with biostable polymer coatings, which release antiproliferative drugs at a controlled rate and total dose. Specific examples of biostable polymers for biostable drug eluting polymer coatings include homopolymers and copolymers, such as poly(ethylene-co-vinyl acetate), poly (vinylidene fluoride-co-hexafluoropropylene) and poly (isobutylene-co-styrene), for example, poly(styrene-b-isobutylene-b-styrene) triblock copolymers (SIBS).

Neurostimulation devices are a known class of medical device, which deliver mild electrical impulses to neural tissue. For example, electrical impulses may be directed to specific sites to treat pain, Parkinson's disease or epileptic seizures, or to enhance sensory function. Specific examples of neurostimulation systems include spinal cord stimulation (SCS) systems, deep brain stimulation (DBS) systems, peripheral nerve stimulation (PNS) systems, cochlear implant systems, retinal implant systems, implantable pacemaker systems, and implantable cardioverter-defibrillators (ICD's). Each of these systems includes a neurostimulator and one or more electrical leads, each containing one or more contacts.

As used herein, a stimulation "lead" is an implantable device that has one or more electrical contacts that deliver current to tissue to be stimulated. A "contact" is a part of the lead which is electrically conductive and is in contact with the body tissue that is to be stimulated. The terms "lead" and "electrode" may be used interchangeably herein and refer to the entire elongate structure that is partially or wholly implanted into the patient. A stimulation lead can include, for example, one or more contacts, an insulating body (also referred to herein as a "lead body"), one or more elongate conductors (e.g., wires) running within at least a portion of the length of the lead body, and any other assembly on or within the lead body. The lead body is typically formed from a polymeric material.

Systems for SCS and DBS generally include a neurostimulator and one or more stimulation leads. Commonly the neurostimulator is an implantable pulse generator (IPG), which holds advanced electronics and a rechargeable battery and generates pain-masking electrical signals.

SCS is a safe and effective therapy that has been in use for over several decades and has helped thousands of people find pain relief. SCS devices may be totally or partially implantable. Commonly, at least the IPG and stimulation lead(s) are implantable. For instance, an IPG may be implanted in the abdomen, upper buttock, or pectoral region of a patient, whereas at least one lead may be implanted under the skin next to the spinal cord. Each lead may contain one or more contacts (e.g., from one to eight contacts or more) that deliver pain-masking electrical signals to the spinal cord. In certain systems, one or more lead extensions are used to electrically connect the stimulation lead to the IPG, which lead extensions may also be implantable.

A DBS device comprises similar components (i.e. an IPG, at least one stimulation lead, and commonly at least one lead extension) and may be utilized to provide a variety of different types of electrical stimulation to reduce the occurrence and/or effects of Parkinson's disease, epileptic seizures, or other undesirable neurological conditions. In this case, the IPG may be implanted, for example, into the pectoral region of the patient and the lead(s) implanted in the brain. One or more lead extensions may be implanted and extend along the patient's neck so as to electrically connect the stimulation lead(s) to the IPG. The distal end of the lead(s) may contain one or more contacts (commonly from four to eight contacts).

The implantation procedures for SCS and DBS devices are reversible, which means even though they are surgically implanted, the devices can be removed by the doctor.

An example of a neural stimulation system 10 which may be used for SCS and/or DBS is shown in FIG. 1. Such a system typically comprises an IPG 12, a lead extension 14, a lead 16 having a contact array 18 including a plurality of contacts 17. The IPG 12 is provided with a connector 5, which accepts the connector end of the lead extension 14. The contacts 17 are arranged as shown in an in-line contact array 18 near the distal end of the lead 16. Other contact array configurations may also be used, such as non-linear and parallel configurations, among others. The IPG 12 generates current pulses that are applied to selected ones of the contacts 17 within the array 18. See Pub. No. US 2007/0168007 to Kuzma. A lead 16 like that shown in FIG. 1 may be made in the following manner, among other methods: Individually insulated wires may be placed loosely within polymer tubing such as silicone, polyurethane, or polytetrafluoroethylene tubing. A platinum contact may be welded at the distal end of each wire, and a controlled spacing may be provided between each contact. Voids between the contacts are then filled with a suitable polymer, such as silicone or polyurethane, using known injection molding techniques. See Pub. No. US 2007/0168004 to Walter.

A cochlear implant system is an implantable electronic device for a patient with severe to profound deafness (e.g., 60-120 dB or more of hearing loss) caused by a sensory deficiency. It has an external component and an internal component that work in concert. The external component typically comprises an externally worn microphone, a sound processor, and a transmitter. The internal component typically comprises a receiver, a neurostimulator, and a neurostimulation lead with one or more electrical contacts (typically 16-24 electrical contacts) that is implanted within a patient's inner ear. In a normal ear, sound waves enter the external ear, vibrate the flexible surface of the eardrum and middle ear bones, and convey sound to the oval window of the inner ear or cochlea. In the cochlea, the vibration is transmitted to the perilymph fluid, causing movement of the hair cells in the cochlea, which convert the motion to electrical signals and transmit the signals to the auditory nerve. In a person with sensory hearing loss, these hair cells may be damaged and unable to transmit the electrical signal to the auditory nerve. A cochlear implant such as that previously described can replace the function of the hair cells, receiving the sound and converting it to an electrical signal to send to the auditory nerve.

FIG. 2 depicts the distal end of one type of a lead 46 that can be used with an implantable cochlear stimulation system. In this example, the lead 46 includes an in-line configuration of sixteen contacts, designated E1, E2, E3, ... E16 disposed at the surface of a polymeric lead body. Electrical contact E1 is the most distal electrical contact, and electrical contact E16 is the most proximal. The more distal electrical contacts, i.e., the electrical contacts having lower numbers such as E1, E2, E3, E4, are the electrical contacts through which stimulation pulses are applied in order to elicit the sensation of lower perceived frequencies. The more proximal electrical contacts, i.e., the electrical contacts having higher numbers such as E13, E14, E15 and E16, are the electrical contacts through which stimulation pulses are applied in order to elicit the sensation of higher perceived frequencies. The particular electrical contact, or combination of electrical contacts, through which stimulation pulses are applied is determined by the speech processing circuitry, which circuitry, inter alia, and in accordance with a selected speech processing strategy, separates the incoming sound signals into frequency bands and analyzes how much energy is contained within each band, thereby enabling it to determine which electrical contacts should receive stimulation pulses. See, e.g., Pub. No. US 2005/0251225 to Faltys et al.

SUMMARY OF THE INVENTION

In various aspects, the present invention is directed to implantable neurostimulation leads and methods for their formation. Such implantable neurostimulation leads typically include (a) at least one electrical contact, (b) at least one elongated conductor in electrical communication with at least one electrical contact and extending along at least a portion of the length of the lead, and (c) a polymeric lead body that supports the contact and encapsulates at least a portion of the length of the elongated conductor.

In one aspect, the implantable neurostimulation leads comprise a block copolymer, for instance, a block copolymer that comprises a polystyrene block and a polyisobutylene block (e.g., SIBS, among others) and, optionally, a therapeutic agent. In some embodiments, the polymeric lead body comprises a block copolymer. In some embodiments, a polymeric layer comprising a block copolymer is disposed over the lead body.

In another aspect, the implantable neurostimulation leads comprise an antioxidant.

In another aspect, at least one electrical contact associated with an implantable neurostimulation lead has an external tissue contacting surface and an internal surface encased by the polymeric lead body, wherein a layer comprising a therapeutic agent is disposed between the internal surface of the contact and the polymeric lead body.

In another aspect, methods of forming implantable neurostimulation leads are provided which comprise (a) providing a mold that has a therapeutic-agent-containing layer comprising a therapeutic agent disposed over its surface and (b) molding the polymeric lead body within the mold.

In another aspect, methods of depositing a material on neurostimulation device lead bodies are provided, which comprise depositing the material over the lead bodies without depositing the material over the electrical contacts.

In various additional aspects, the present invention is directed to medical devices having silicone-containing regions with overlying polymeric layers and to methods of forming the same.

In one aspect, medical devices are provided that comprise (a) a region comprising silicone and (b) a polymeric layer comprising a block copolymer disposed over the region.

In another aspect, medical devices are provided that comprise (a) a region comprising silicone, (b) a polymeric layer comprising a first polymer disposed over the region, the first polymer comprising a first monomer and (c) a tie layer between the region and the polymeric layer that comprises a second polymer. The second polymer comprises a silicon-containing monomer, the first monomer, or both, wherein the first and second polymers are different.

In another aspect, medical devices are provided that comprise (a) a first region comprising silicone, (b) a polymeric layer comprising a first polymer disposed over the silicone, and (c) a tie layer between the first region and the polymeric layer, wherein the tie layer comprises an organosilicon compound.

In another aspect, the present invention provides methods of improving the adhesion between a first region of medical devices that comprises silicone and a polymeric layer comprising a polymer that this disposed over the first region. In accordance with one embodiment, such methods comprise: swelling the first region with a first solvent; applying a solution comprising the polymer and a second solvent to the swelled silicone, wherein the first solvent and the second solvent may be the same or different; and evaporating the solvent to form the polymeric layer. In accordance with another embodiment, such methods comprise texturing the surface of the first region to form a textured surface and applying the polymeric layer to the textured surface.

In another aspect, the present invention provides methods of improving the adhesion between a first region of a medical device that comprises partially crosslinked silicone and a polymeric layer comprising a polymer that is disposed over the first region. The methods comprise applying the polymeric layer to the first region and then crosslinking the silicone.

These and other aspects and embodiments, as well as various advantages of the present invention will become immediately apparent to those of ordinary skill in the art upon review of the Detailed Description and any claims to follow.

BRIEF DESCRIPTION OF THE DRAWINGS

FIG. 6 is a side view schematically illustrating a direct deposit method in accordance with an embodiment of the present invention.

FIG. 8 is a side view schematically illustrating a drop-on-demand inkjet method in accordance with an embodiment of the present invention.

DETAILED DESCRIPTION OF THE INVENTION

Figure 1:
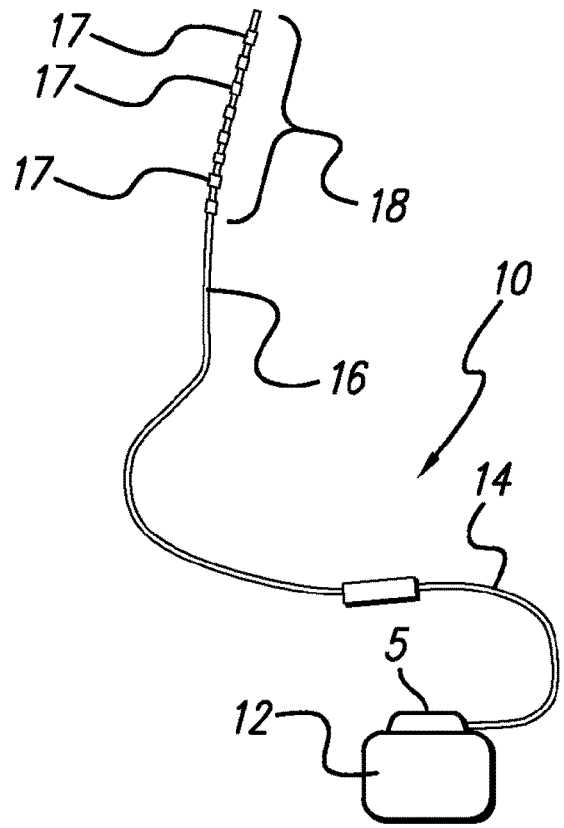
FIG. 1 is a schematic illustration of a neurostimulation system in accordance with the prior art.
Figure 2:
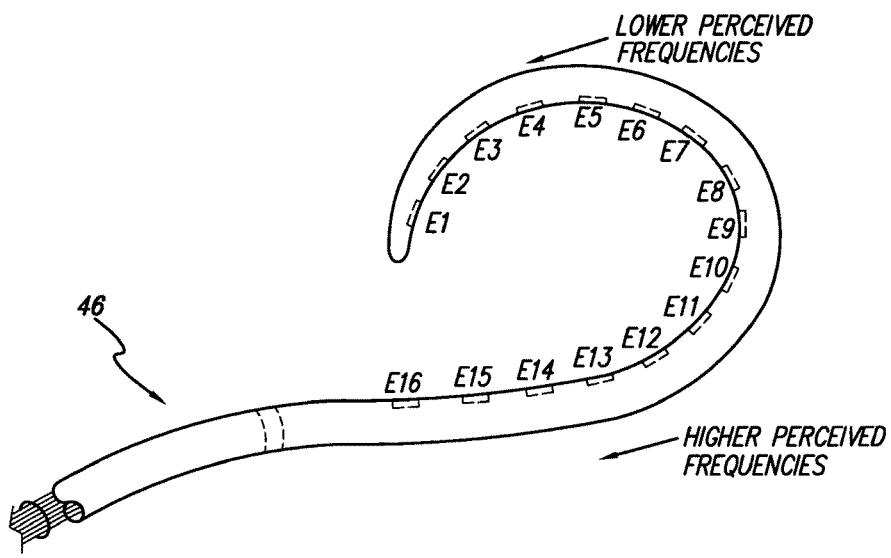
FIG. 2 is a schematic illustration of a cochlear lead in accordance with the prior art.

According to one aspect of the invention, improved polymeric materials are provided for use in implantable or insertable medical devices. Such polymeric materials may correspond, for example, to a device, a device component or device coating.

In various embodiments, the present invention provides improved polymeric materials for use in neurostimulation systems. As noted above, these systems typically comprise a neurostimulator for generating suitable electrical signals and one or more neurostimulation leads. These systems may also optionally comprise further components such as lead extensions, transmitters/receivers, sensors, and so forth. A lead for these systems will typically comprise (a) at least one electrical contact for delivering the electrical signal to tissue that is amenable to electrical stimulation, typically a metallic contact formed from a corrosion resistant metal or metal alloy, for example, a noble metal such as gold, platinum, or palladium or alloys of the same, among other possibilities, (b) at least one elongate conductor, typically a conductive metallic interconnecting wire, which may be, for example, formed of a metal such as copper, silver, gold, platinum, or palladium or an alloy of the same, among other conductors, for transmitting signals between the neurostimulator and the contact(s) through at least a portion of the lead and (c) a lead body which supports the contacts and encloses the interconnecting wires within the lead.

In accordance with various embodiments of the invention, improved polymeric materials are provided for use in lead bodies and in coatings for the same.

In accordance with other embodiments, improved polymeric materials are provided for at least partially enclosing (e.g., as a primary polymeric enclosure material or as a coating for the same) implantable devices in addition to leads, including, for example, implantable lead extensions, neurostimulators, receivers, and so forth.

Polymeric materials in the various devices of the invention may provide one or more of the following functions, among others: (a) a biocompatible device surface, (b) therapeutic agent release, (c) mechanical support, and (d) electrical insulation.

Polymeric Materials

As used herein, a "polymeric material" is one that contains one or more types of polymers, for example, containing from 50 wt % to less to 75 wt % to 90 wt % to 95 wt % to 97 wt % to 99 wt % or more polymers. Two polymers are of different "types" where the polymers have a different monomer content (i.e., one polymer contains a monomer that is not found in the other polymer, e.g., polystyrene vs. polyisobutylene, polystyrene vs. poly(isobutylene-alt-styrene), etc.).

In addition to one or more types of polymers, polymeric materials for use in the invention may further comprise a number of additional agents in certain embodiments, including therapeutic agents, among other possibilities. "Therapeutic agents," "drugs," "pharmaceutically active agents," "biologically active materials," and other related terms may be used interchangeably in the present disclosure.

As used herein, "polymers" are molecules containing multiple copies (e.g., 5 to 10 to 100 to 1000 to 10,000 or more copies) of one or more constitutional units, commonly referred to as "monomers". As used herein, the "monomers" may refer to free monomers or to those that are incorporated into polymers, with the distinction being clear from the context in which the term is used. Polymers may take on a number of configurations, which may be selected, for example, from cyclic, linear and branched configurations. Branched configurations include star-shaped configurations (e.g., configurations in which three or more chains emanate from a single branch point, such as a seed molecule), comb configurations (e.g., configurations having a main chain and a plurality of side chains), dendritic configurations (e.g., arborescent and hyperbranched polymers), networked (e.g., crosslinked) configurations, and so forth.

Unless indicated otherwise, polymer molecular weights set forth herein are number average molecular weights (Mn).

As used herein, "homopolymers" are polymers that contain multiple copies of a single constitutional unit. "Copolymers" are polymers that contain multiple copies of at least two dissimilar constitutional units, examples of which include random, statistical, gradient, periodic (e.g., alternating) and block copolymers. As used herein, "block copolymers" are copolymers that contain two or more differing polymer blocks, which differ because a constitutional unit (i.e., a monomer) is found in one polymer block that is not found in another polymer block. As used herein, a "polymer block" is a grouping of constitutional units (e.g., 5 to 10 to 25 to 50 to 100 to 250 to 500 to 1000 or more units). Blocks can be branched or unbranched. Blocks can contain a single type of constitutional unit ("homopolymer blocks") or multiple types of constitutional units ("copolymer blocks") which may be provided, for example, in a random, statistical, gradient, or periodic (e.g., alternating) distribution.

Polymeric materials for use in the medical devices of the present invention may vary widely, depending on the particular embodiment, and may be selected, for example, from suitable members of the following and blends thereof, among others: polycarboxylic acid polymers and copolymers including polyacrylic acids; acetal polymers and copolymers; acrylate and methacrylate polymers and copolymers (e.g., n-butyl methacrylate); cellulosic polymers and copolymers, including cellulose acetates, cellulose nitrates, cellulose propionates, cellulose acetate butyrates, cellophanes, rayons, rayon triacetates, and cellulose ethers such as carboxymethyl celluloses and hydroxyalkyl celluloses; polyoxymethylene polymers and copolymers; polyimide polymers and copolymers such as polyether block imides and polyether block amides, polyamidimides, polyesterimides, and polyetherimides; polysulfone polymers and copolymers including polyarylsulfones and polyethersulfones; polyamide polymers and copolymers including nylon 6,6, nylon 12, polycaprolactams and polyacrylamides; resins including alkyd resins, phenolic resins, urea resins, melamine resins, epoxy resins, allyl resins and epoxide resins; polycarbonates; polyacrylonitriles; polyvinylpyrrolidones (cross-linked and otherwise); polymers and copolymers of vinyl monomers including polyvinyl alcohols, polyvinyl halides such as polyvinyl chlorides, ethylene-vinyl acetate copolymers (EVA), polyvinylidene chlorides, polyvinyl ethers such as polyvinyl methyl ethers, polystyrenes, styrene-maleic anhydride copolymers, vinyl-aromatic-olefin copolymers, including styrene-butadiene copolymers, styrene-ethylene-butylene copolymers (e.g., a polystyrene-polyethylene/butylene-polystyrene (SEBS) copolymer, available as Kraton® G series polymers), styrene-isoprene copolymers (e.g., polystyrene-polyisoprene-polystyrene), acrylonitrile-styrene copolymers, acrylonitrile-butadiene-styrene copolymers, styrene-butadiene copolymers and styrene-isobutylene copolymers (e.g., polyisobutylene-polystyrene and polystyrene-polyisobutylene-polystyrene triblock copolymers such as those disclosed in U.S. Pat. No. 6,545,097 to Pinchuk), polyvinyl ketones, polyvinylcarbazoles, and polyvinyl esters such as polyvinyl acetates; polybenzimidazoles; ethylene-methacrylic acid copolymers and ethylene-acrylic acid copolymers, where some of the acid groups can be neutralized with either zinc or sodium ions (commonly known as ionomers); polyalkyl oxide polymers and copolymers including polyethylene oxides (PEO); polyesters including polyethylene terephthalates and aliphatic polyesters such as polymers and copolymers of lactide (which includes lactic acid as well as d-,l- and meso lactide), epsilon-caprolactone, glycolide (including glycolic acid), hydroxybutyrate, hydroxyvalerate, para-dioxanone, trimethylene carbonate (and its alkyl derivatives), 1,4-dioxepan-2-one, 1,5-dioxepan-2-one, and 6,6-dimethyl-1,4-dioxan-2-one (a copolymer of poly(lactic acid) and poly(caprolactone) is one specific example); polyether polymers and copolymers including polyarylethers such as polyphenylene ethers, polyether ketones, polyether ether ketones; polyphenylene sulfides; polyisocyanates; polyolefin polymers and copolymers, including polyalkylenes such as polypropylenes, polyethylenes (low and high density, low and high molecular weight), polybutylenes (such as polybut-1-ene and polyisobutylenes), polyolefin elastomers (e.g., santoprene), ethylene propylene diene monomer (EPDM) rubbers, poly-4-methyl-pen-1-enes, ethylene-alpha-olefin copolymers, ethylene-methyl methacrylate copolymers and ethylene-vinyl acetate copolymers; fluorinated polymers and copolymers, including polytetrafluoroethylenes (PTFE), poly(tetrafluoroethylene-co-hexafluoropropene) (FEP), modified ethylene-tetrafluoroethylene copolymers (ETFE), and polyvinylidene fluorides (PVDF); silicone polymers and copolymers; thermoplastic polyurethanes (TPU); elastomers such as elastomeric polyurethanes and polyurethane copolymers (including block and random copolymers that are polyether based, polyester based, polycarbonate based, aliphatic based, aromatic based and mixtures thereof; examples of commercially available polyurethane copolymers include Bionate®, Carbothane®, Tecoflex®, Tecothane®, Tecophilic®, Tecoplast®, Pellethane®, Chronothane® and Chronoflex®); p-xylylene polymers; polyiminocarbonates; copoly(ether-esters) such as polyethylene oxide-polylactic acid copolymers; polyphosphazines; polyalkylene oxalates; polyoxaamides and polyoxaesters (including those containing amines and/or amido groups); polyorthoesters; biopolymers, such as polypeptides, proteins, polysaccharides and fatty acids (and esters thereof), including fibrin, fibrinogen, collagen, elastin, chitosan, gelatin, starch, glycosaminoglycans such as hyaluronic acid; as well as copolymers of the above.

As indicated above, in some embodiments, polymers for use in the present invention are block copolymers. Polymer blocks for use in block copolymers for the practice of the invention include low glass transition temperature (Tg) polymer blocks and high Tg polymer blocks. As used herein, a "low Tg polymer block" is one that displays a Tg that is below body temperature (37° C.), more typically from 35° C. to 20° C. to 0° C. to −25° C. to −50° C. or below. Conversely, as used herein, a "high Tg polymer block" is one that displays a Tg that is above body temperature, more typically from 40° C. to 50° C. to 75° C. to 100° C. or above. Tg can be measured by differential scanning calorimetry (DSC). As used herein, a "low Tg monomer" is one that displays a Tg that is below body temperature when in homopolymers form, while a "high Tg monomer" is one that displays a Tg that is above body temperature when in homopolymers form.

Typical molecular weights for high Tg polymer blocks may vary widely and range, for example, from 1 kDaltons or less to 2.5 kDaltons to 5.0 kDaltons to 10 kDaltons to 25 kDaltons to 50 kDaltons to 100 kDaltons to 200 kDaltons or more. Typical molecular weights for low Tg polymer blocks may vary widely and also range, for example, from 1 kDaltons or less to 2.5 kDaltons to 5.0 kDaltons to 10 kDaltons to 25 kDaltons to 50 kDaltons to 100 kDaltons to 200 kDaltons or more.

Specific examples of low Tg polymer blocks include homopolymer and copolymer blocks containing one or more of the following low Tg monomers (listed along with published Tg's for homopolymers of the same): (1) unsubstituted and substituted alkene monomers including ethylene, propylene (Tg −8 to −13° C.), isobutylene (Tg −73° C.), 1-butene (Tg −24° C.), 4-methyl pentene (Tg 29° C.), 1-octene (Tg −63° C.) and other α-olefins, dienes such as 1,3-butadiene, 2-methyl-1,3-butadiene (isoprene), 2,3-dimethyl-1,3-butadiene, 2-ethyl-1,3-butadiene, 1,3-pentadiene, 2-methyl-1,3-pentadiene, 4-butyl-1,3-pentadiene, 2,3-dibutyl-1,3-pentadiene, 2-ethyl-1,3-pentadiene, 1,3-hexadiene, 1,3-octadiene and 3-butyl-1,3-octadiene, and halogenated alkene monomers including vinylidene chloride (Tg −18° C.), vinylidene fluoride (Tg −40° C.), hexafluoropropylene, cis-chlorobutadiene (Tg −20° C.), and trans-chlorobutadiene (Tg −40° C.); (2) acrylic monomers including: (a) alkyl acrylates such as methyl acrylate (Tg 10° C.), ethyl acrylate (Tg −24° C.), propyl acrylate, isopropyl acrylate (Tg −11° C., isotactic), butyl acrylate (Tg −54° C.), sec-butyl acrylate (Tg −26° C.), isobutyl acrylate (Tg −24° C.), cyclohexyl acrylate (Tg 19° C.), 2-ethylhexyl acrylate (Tg −50° C.), dodecyl acrylate (Tg −3° C.) and hexadecyl acrylate (Tg 35° C.), (b) arylalkyl acrylates such as benzyl acrylate (Tg 6° C.), (c) alkoxyalkyl acrylates such as 2-ethoxyethyl acrylate (Tg −50° C.) and 2-methoxyethyl acrylate (Tg −50° C.), (d) halo-alkyl acrylates such as 2,2,2-trifluoroethyl acrylate (Tg −10° C.) and (e) cyano-alkyl acrylates such as 2-cyanoethyl acrylate (Tg 4° C.); (3) methacrylic monomers including (a) alkyl methacrylates such as butyl methacrylate (Tg 20° C.), hexyl methacrylate (Tg −5° C.), 2-ethylhexyl methacrylate (Tg −10° C.), octyl methacrylate (Tg −20° C.), dodecyl methacrylate (Tg −65° C.), hexadecyl methacrylate (Tg 15° C.) and octadecyl methacrylate (Tg −100° C.) and (b) aminoalkyl methacrylates such as diethylaminoethyl methacrylate (Tg 20° C.) and 2-tert-butyl-aminoethyl methacrylate (Tg 33° C.); (4) vinyl ether monomers including (a) alkyl vinyl ethers such as methyl vinyl ether (Tg −31° C.), ethyl vinyl ether (Tg −43° C.), propyl vinyl ether (Tg −49° C.), butyl vinyl ether (Tg −55° C.), isobutyl vinyl ether (Tg −19° C.), 2-ethylhexyl vinyl ether (Tg −66° C.) and dodecyl vinyl ether (Tg −62° C.); (5) cyclic ether monomers including tetrahydrofuran (Tg −84° C.), trimethylene oxide (Tg −78° C.), ethylene oxide (Tg −66° C.), propylene oxide (Tg −75° C.), methyl glycidyl ether (Tg −62° C.), butyl glycidyl ether (Tg −79° C.), allyl glycidyl ether (Tg −78° C.), epibromohydrin (Tg −14° C.), epichlorohydrin (Tg −22° C.), 1,2-epoxybutane (Tg −70° C.), 1,2-epoxyoctane (Tg −67° C.) and 1,2-epoxydecane (Tg −70° C.); (6) ester monomers (other than the above acrylates and methacrylates) including ethylene malonate (Tg −29° C.), vinyl acetate (Tg 30° C.), and vinyl propionate (Tg 10° C.); and (7) siloxane monomers including dimethylsiloxane (Tg −127° C.), diethylsiloxane, methylethylsiloxane, and methylphenylsiloxane (Tg −86° C.).

Specific examples of high Tg polymer blocks include homopolymer and copolymer blocks containing one or more of the following high Tg monomers: (1) vinyl aromatic monomers including (a) unsubstituted vinyl aromatics, such as styrene (Tg 100° C.) and 2-vinyl naphthalene (Tg 151° C.), (b) vinyl substituted aromatics such as alpha-methyl styrene, and (c) ring-substituted vinyl aromatics including ring-alkylated vinyl aromatics such as 3-methylstyrene (Tg 97° C.), 4-methylstyrene (Tg 97° C.), 2,4-dimethylstyrene (Tg 112° C.), 2,5-dimethylstyrene (Tg 143° C.), 3,5-dimethylstyrene (Tg 104° C.), 2,4,6-trimethylstyrene (Tg 162° C.), and 4-tert-butylstyrene (Tg 127° C.), ring-alkoxylated vinyl aromatics, such as 4-methoxystyrene (Tg 113° C.) and 4-ethoxystyrene (Tg 86° C.), ring-halogenated vinyl aromatics such as 2-chlorostyrene (Tg 119° C.), 3-chlorostyrene (Tg 90° C.), 4-chlorostyrene (Tg 110° C.), 2,6-dichlorostyrene (Tg 167° C.), 4-bromostyrene (Tg 118° C.) and 4-fluorostyrene (Tg 95° C.), ring-ester-substituted vinyl aromatics such as 4-acetoxystyrene (Tg 116° C.), ring-hydroxylated vinyl aromatics such as 4-hydroxystyrene (Tg 174° C.), ring-amino-substituted vinyl aromatics including 4-amino styrene, ring-silyl-substituted styrenes such as p-dimethylethoxy siloxy styrene, unsubstituted and substituted vinyl pyridines such as 2-vinyl pyridine (Tg 104° C.) and 4-vinyl pyridine (Tg 142° C.), and other vinyl aromatic monomers such as vinyl carbazole (Tg 227° C.) and vinyl ferrocene (Tg 189° C.); (2) other vinyl monomers including (a) vinyl esters such as vinyl benzoate (Tg 71° C.), vinyl 4-tert-butyl benzoate (Tg 101° C.), vinyl cyclohexanoate (Tg 76° C.), vinyl pivalate (Tg 86° C.), vinyl trifluoroacetate (Tg 46° C.), vinyl butyral (Tg 49° C.), (b) vinyl amines, (c) vinyl halides such as vinyl chloride (Tg 81° C.) and vinyl fluoride (Tg 40° C.), (d) alkyl vinyl ethers such as tert-butyl vinyl ether (Tg 88° C.) and cyclohexyl vinyl ether (Tg 81° C.), and (e) other vinyl compounds such as vinyl pyrrolidone; (3) other aromatic monomers including acenaphthalene (Tg 214° C.) and indene (Tg 85° C.); (4) methacrylic monomers including (a) methacrylic acid anhydride (Tg 159° C.), (b) methacrylic acid esters (methacrylates) including (i) alkyl methacrylates such as methyl methacrylate (Tg 105-120° C.), ethyl methacrylate (Tg 65° C.), isopropyl methacrylate (Tg 81° C.), isobutyl methacrylate (Tg 53° C.), t-butyl methacrylate (Tg 118° C.) and cyclohexyl methacrylate (Tg 92° C.), (ii) aromatic methacrylates such as phenyl methacrylate (Tg 110° C.) and including aromatic alkyl methacrylates such as benzyl methacrylate (Tg 54° C.), (iii) hydroxyalkyl methacrylates such as 2-hydroxyethyl methacrylate (Tg 57° C.) and 2-hydroxypropyl methacrylate (Tg 76° C.), (iv) additional methacrylates including isobornyl methacrylate (Tg 110° C.) and trimethylsilyl methacrylate (Tg 68° C.), and (c) other methacrylic-acid derivatives including methacrylonitrile (Tg 120° C.); (5) acrylic monomers including (a) certain acrylic acid esters such as tert-butyl acrylate (Tg 43-107° C.), hexyl acrylate (Tg 57° C.) and isobornyl acrylate (Tg 94° C.); (b) other acrylic-acid derivatives including acrylonitrile (Tg 125° C.); and (c) siloxane monomers including diphenylsiloxane.

A few examples of block copolymer structures include the following, among others: (a) block copolymers having alternating blocks of the type $(AB)_m$, $B(AB)_m$ and $A(BA)_m$ where A is a first polymer block, B is a second polymer block that is different from the first polymer block, and m is a positive whole number of 1 or more, and (b) block copolymers having multi-arm architectures, such as $X(BA)_n$, and $X(AB)_n$, where n is a positive whole number of 2 or more and X is a hub species (e.g., an initiator molecule residue, a residue of a molecule to which preformed polymer chains are attached, etc.). In addition to the hub species mentioned above, copolymers such as those above can contain a variety of other non-polymer-chain species, which are commonly present in copolymers, including capping molecules, among others. Note that non-polymer species, such as hub species, linking species, etc. are generally ignored in describing block copolymer morphology, for example, with $X(BA)_2$ being designated as an ABA triblock copolymer and $X(BA)_3$ being referred to as a star polymer with a B midblock and three A endblocks. Other examples of block copolymers include comb copolymers having a B chain backbone and multiple A side chains, as well as comb copolymers having an A chain backbone and multiple B side chains.

In some embodiments, the A blocks in the above formulas are high Tg polymer blocks and the B blocks in the above formulas are low Tg polymer blocks, numerous examples of high and low Tg polymer blocks are set forth above.

Thermoplastic elastomers include various block copolymers having at least two high Tg blocks (also known as hard blocks) separated by at least one low Tg block (also known as soft blocks or elastomeric blocks). Specific examples include the following (where A is a high Tg block and B is a low Tg block), among others: ABA triblock copolymers, $X(BA)_n$ star copolymers where n is a positive whole number of 3 or more and X is a hub species, and comb copolymers having a B chain backbone and multiple A side chains. The high Tg end/side blocks of such polymers are known to phase separate from the low Tg block mid/main block to supply physical crosslinks to the polymer. These physical crosslinks provide strength to the copolymer.

Poly(styrene-b-isobutylene-b-styrene) tri-block copolymer (SIBS) is an example of such a polymer and has been shown to have vascular compatibility. See, e.g., S. V. Ranade et al., *Acta Biomaterialia* 1 (2005) 137-144. Other specific examples of thermoplastic block copolymers include those described in R. Richard et al., *Biomacromolecules*, 6 (2005) 3410-3418, specifically, poly(methyl methacrylate-b-n-butyl acrylate-b-methyl methacrylate) (MBAM), poly(methyl methacrylate-b-lauryl acrylate-b-methyl methacrylate), poly (isobornyl acrylate-b-lauryl acrylate-b-isobornyl acrylate), poly(isobornyl acrylate-b-n-butyl acrylate-b-isobornyl acrylate), poly(styrene-b-lauryl acrylate-b-styrene), poly(styrene-b-n-butyl acrylate-b-styrene), poly[(styrene-co-acrylonitrile)-b-n-butyl acrylate-b-(styrene-co-acrylonitrile)] and a three-arm star copolymer with a poly-n-butyl acrylate midblock and polystyrene endblocks.

In certain embodiments, polymers for use in the present invention include polymers that contain one or more hydrophilic polymer blocks. For example, one or more hydrophilic blocks (e.g., selected from the hydrophilic blocks described elsewhere herein, among others) may be attached to one of the above polymers (e.g., to the ends of and/or along the length of the polymer). As a more specific example, one or more hydrophilic blocks may be attached to the ends of or along the length of one of the above ABA block copolymers described above. For instance, hydrophilic blocks may be attached to the ends of a SIBS block copolymer (e.g., using allyl-hydride linking chemistry such as that described below, among other possibilities), allowing the hydrophilic/hydrophobic balance of the copolymer to be controlled.

Thus, in certain embodiments, polymers for use in the present invention include block copolymers that contain one or more hydrophilic polymer blocks and one or more hydrophobic polymer blocks.

As a further example, the A blocks in the above-described block copolymer structures may be hydrophilic blocks and the B blocks may be hydrophobic blocks. This allows one to, for example, control the hydrophilic/hydrophobic balance of the copolymer, which in turn will depend upon the particular monomers selected to form the A and B blocks as well as the relative lengths of the A and B blocks.

Hydrophilic polymer blocks may be selected, for example, from hydrophilic homopolymer and copolymer blocks containing one or more of the following monomers, among others: vinyl pyrrolidone, vinyl alcohol, hydroxyethyl methacrylate, methyl methacrylate, hydroxystyrene, methyl vinyl ether, ethylene oxide, and acidic monomers and salts thereof (e.g., ammonium, potassium, sodium, etc. salts) such as methacrylic acid and salts thereof, acrylic acid and salts thereof, and vinyl sulfonic acid and salts thereof. Further examples include sulfonated polymer blocks such as poly (vinylsulfonate) blocks, sulfonated polystyrene blocks, and sulfonated poly(tetrafluoroethylene) blocks, among others.

The hydrophobic blocks may be selected, for example, from hydrophobic homopolymer and copolymer blocks containing one or more of the following monomers, among others: olefins such as ethylene, propylene and isobutylene, fluorinated monomers such as vinylidene fluoride, trifluoroethylene, chlorotrifluoroethylene, tetrafluoroethylene, hexafluoropropene, fluorinated vinyl ether and perfluoromethyl vinyl ether, higher alkyl acrylates and methacrylates (e.g., those with alkyl groups of four carbons or more), including n-butyl acrylate and lauryl acrylate, polyvinyl aromatic monomers such as polystyrene, and siloxane monomers such as dimethylsiloxane, methylphenylsiloxane, and diphenylsiloxane.

Specific examples of polymers having a combination of hydrophilic and hydrophobic blocks include poly(methyl methacrylate-b-isobutylene-b-methyl methacrylate), poly (hydroxyethyl methacrylate-b-isobutylene-b-hydroxyethyl methacrylate), poly(hydroxystyrene-b-isobutylene-b-hydroxystyrene), and poly(cyclohexyl vinyl ether-stat-vinyl alcohol)-b-polyisobutylene-b-poly(cyclohexyl vinyl ether-stat-vinyl alcohol) triblock copolymers. See, e.g., J. Cho et al., *Biomacromolecules,* 7 (2006) 2997-3007, L. Sipos et al., *Biomacromolecules* 6 (2005) 2570-2582, Y. Zhou et al., *Macromolecules,* 38 (2005) 8183-8191. Further examples include poly(methyl methacrylate-b-n-butyl acrylate-b-methyl methacrylate) (MBAM) and poly(methyl methacrylate-b-lauryl acrylate-b-methyl methacrylate), among many others.

Therapeutic Agents and Therapeutic Polymers

As previously indicated, in some embodiments, medical devices in accordance with the invention may also further comprise one or more therapeutic agents, which therapeutic agents may be released from the device upon implantation or insertion into a subject.

For example, in some embodiments, polymeric materials in the devices of the invention may be employed as reservoirs for one or more therapeutic agents (e.g., the therapeutic agent may be blended with the polymeric material, etc.). The therapeutic-agent-containing polymeric materials may be biostable polymeric materials (e.g., those that remain associated with the device after implantation) or bioerodable polymeric materials (e.g., those that do not remain associated with the device after implantation, for example, because the polymeric materials become dissolved and/or biodegraded in vivo). The therapeutic-agent-containing polymeric material may correspond, for instance, to a device, device component or device coating, among other possibilities. Suitable polymers for use in such therapeutic-agent-containing polymeric materials may be selected, for example, from the various homopolymers and copolymers described above, among others.

In some embodiments, the therapeutic-agent-containing polymeric material may correspond to a coating for a medical device. Such coatings typically range in thickness from 1 micron or less to 2 microns to 5 microns to 10 microns to 20 microns to 50 microns to 100 microns or more, among other possible thicknesses.

In some embodiments, the therapeutic-agent-containing polymeric material may correspond to a lead body, to an insulating layer for a lead extension, or to a casing material for a neurostimulator, among many other possibilities.

In other embodiments, a therapeutic agent may be released independently of a polymeric material.

A wide variety of therapeutic agents may be released from the devices of the present invention. A few examples are given below for various neurostimulation devices in accordance with the invention, but it should be understood that the invention is not so limited.

As a first example, current cochlear implant technology typically destroys some or all of the residual hearing that a patient may have prior to surgery. The lead insertion procedure can result in a series of negative physiological effects including acute inflammation, fibrotic encapsulation and apoptosis. Minimization of these effects, may improve the likelihood of residual hearing preservation. Moreover, reduced fibrotic encapsulation may provide for improved device performance and may make it easier to remove the device (e.g., for re-implantation or replacement). In order to address these effects, a suitable pharmaceutical agent is released in certain embodiments of the invention. Moreover, a biocompatible/pro-healing surface may be established as well (e.g., by employing a suitable biocompatible polymer as a carrier material for the therapeutic agent by blending the biocompatible polymer with the therapeutic agent).

As another example, device related infection is a common, potentially reducible, serious adverse event associated with implantable medical devices, including neurostimulation systems such as SCS or DBS systems. The IPG or the IPG pocket and the neurostimulation leads are common infection sites. Reducing infections is important for various reasons. One is that the treatment of an established infection often involves temporary or permanent removal of the device thus disrupting therapy. This in turn causes inconvenience and expense, not to mention the further opportunities for infection. Currently physicians use aseptic techniques in the operating room and use abundant prophylactic antibiotics to reduce the rate of infection. In order to further minimize infection, a suitable pharmaceutical agent may be released in certain embodiments of the invention.

As yet another example, promoting selective anchoring may reduce migration observed in the field post implantation (e.g., at places within the epidural space for SCS, etc.). In some embodiments of the invention, a suitable therapeutic agent may be released, which promotes selective anchoring that is sufficient to prevent lateral and longitudinal migration as a result of normal activities, while at the same time allowing for the removal of the lead for lead revision by rotation of the lead body.

Thus, therapeutic agents which may be released from various devices in accordance with the present invention such as neurostimulation devices, among others, include therapeutic agents that are effective to reduce infection and/or agents that are effective of promote selective anchoring and/or agents that are effective to promote local healing, including those effective to reduce foreign body response and/or implant trauma (e.g., glutamate exotoxicity, fibrotic encapsulation, oxidative stress, apoptosis, etc.).

In some embodiments of the invention, antibacterial agents may be used as therapeutic agents in neurostimulation systems, among other devices. Examples of antibacterial agents include penicillins (e.g., penicillin g, methicillin, oxacillin, ampicillin, amoxicillin, ticarcillin, etc.), cephalosporins (e.g., cephalothin, cefazolin, cefoxitin, cefotaxime, cefaclor, cefoperazone, cefixime, ceftriaxone, cefuroxime, etc.), cephamycins (e.g., cefbuperazone, cefmetazole, cefminox, cefetan, cefoxitin, etc.), carbapenems (e.g., imipenem, metropenem, etc.), monobactems (e.g., aztreonem, etc.), ansamycins (e.g., rifamide, rifampin, rifamycin, rifapentine, rifaximin, etc.), lincosamides (e.g., clindamycin, lincomycin, etc.), beta-lactams, carbacephems (e.g., loracarbef, etc.), glycopeptides (e.g., vancomycin, teichoplanin, etc.), bacitracin, polymyxins, colistins, fluoroquinolones (e.g., norfloxacin, lomefloxacin, fleroxacin, ciprofloxacin, enoxacin, trovafloxacin, gatifloxacin, etc.), sulfonamides (e.g., sulfamethoxazole, sulfanilamide, etc.), oxacephems (e.g., flomoxef, moxolactam, etc.), diaminopyrimidines (e.g., trimethoprim, etc.), rifampin, ritipenem, cycloserine, mupirocin, tuberin, aminoglycosides (e.g., streptomycin, neomycin, netilmicin, tobramycin, gentamicin, amikacin, etc.), tetracyclines (e.g., tetracycline, doxycycline, demeclocycline, minocycline, etc.), amphenicols (e.g., azidamfenicol, chloramphenicol, florfenicol, thiamphenicol,) spectinomycin, macrolides (e.g., erythromycin, azithromycin, clarithromycin, dirithromycin, troleandomycin, etc.), and oxazolidinones (e.g., linezolid, etc.), among others, as well as combinations and pharmaceutically acceptable salts, esters and other derivatives of the same.

In some embodiments of the invention, steroids may be used as therapeutic agents in neurostimulation systems, among other devices. For example, steroids have a history of use in the field of otology, having been used by physicians by dipping leads in steroid solutions prior to insertion. Steroids are anti-inflammatory and thus may reduce the inflammatory processes leading to necrosis and apoptosis. Steroids have been shown to protect animal models against noise-induced trauma, and they have been shown to prevent increases in lead electrical impedance. Without wishing to be bound by theory, it is believed that steroids may reduce inflammatory processes that lead to cell necrosis and death, thereby reducing long term fibrotic encapsulation of the lead (as well as other adverse effects based on foreign body reactions). This, in turn, may result in reduced stimulation power requirements, lower behavioral thresholds and reduced crosstalk via current spread. This may also reduce the difficulty of removing medical device component such a leads. In the case of cochlear implants, this may further increase the likelihood that existing hearing will be preserved.

Currently used steroid compounds for local inner ear applications include methylprednisolone, triamcinolone, and dexamethasone. Dexamethasone (DEX) is a synthetic glucocorticoid and has anti-inflammatory action. It is believed to act through the glucocorticoid receptors. It has also been shown that dexamethazone gives the best results of the three corticosteroids in inhibiting fibroblast outgrowth from P-4 spiral ganglion explants and supporting neuritogenesis from the auditory neurons. A. Furze et al., "Dexamethasone and methylprednisolone do not inhibit neuritic outgrowth while inhibiting outgrowth of fibroblasts from spiral ganglion explants," *Acta Oto-Laryngologica*, 2008, 128(2), 122-127.

Further specific examples of steroids (other than methylprednisolone, triamcinolone, and dexamethasone) include glucocorticoids such as 21-acetoxyprefnenolone, alclometasone, algestone, amcinonide, beclomethasone, betamethasone, budesonide, chloroprednisone, clobetasol, clobetasone, clocortolone, cloprednol, corticosterone, cortisone, cortivazol, deflazacort, desonide, desoximetasone, diflorasone, diflucortolone, difluprednate, enoxolone, fluazacort, fluclorinide, flumethasone, flunisolide, fluocinolone acetonide, fluocinonide, fluocortin butyl, fluocortolone, fluorometholone, fluperolone acetate, fluprednidene acetate, fluprednisolone, flurandrenolide, fluticasone propionate, formocortal, halcinonide, halobetasol propionate, halometasone, halopredone acetate, hydrocortamate, hydrocortisone, loteprednol etabonate, mazipredone, medrysone, meprednisone, mometasone furcate, paramethasone, prednicarbate, prednisolone, prednisolone 25-diethylaminoacetate, prednisone sodium phosphate, prednisone, prednival, prednylidene, rimexolone, tixocortol, triamcinolone acetonide, triamcinolone benetonide, and triamcinolone hexacetonide, as well as combinations and pharmaceutically acceptable salts, esters and other derivatives of the same.

Examples of anti-inflammatory drugs other than steroids include NSAIDs (non-steroidal anti-inflammatory drugs). In some embodiments of the invention, NSAIDs may be used as therapeutic agents in neurostimulation systems, among other devices. Examples of NSAIDs include aspirin, diflunisal, salsalate, ibuprofen, ketoprofen, naproxen indomethacin, celecoxib, valdecoxib, diclofenac, etodolac, fenoprofen, flurbiprofen, ketorolac, meclofenamate, meloxicam, nabumetone, naproxen, oxaprozin, piroxicam, sulindac, tolmetin, and valdecoxib, among others, as well as combinations and pharmaceutically acceptable salts, esters and other derivatives of the same.

In some embodiments of the invention, antiproliferative/antineoplastic agents may be used as therapeutic agents in neurostimulation systems, among other devices. Such agent may act to reduce fibrotic encapsulation, among other effects. Examples of antiproliferative/antineoplastic agents include antimetabolites such as purine analogs (e.g., 6-mercaptopurine or cladribine, which is a chlorinated purine nucleoside analog, etc.), pyrimidine analogs (e.g., cytarabine, 5-fluorouracil, etc.) and methotrexate, nitrogen mustards, alkyl sulfonates, ethylenimines, antibiotics (e.g., daunorubicin, doxorubicin, etc.), nitrosoureas, cisplatin, agents affecting microtubule dynamics (e.g., vinblastine, vincristine, colchicine, Epo D, paclitaxel, epothilone, etc.), caspase activators, proteasome inhibitors, angiogenesis inhibitors (e.g., endostatin, angiostatin, squalamine, etc.), sirolimus, everolimus, tacrolimus, zotarolimus, biolimus, cerivastatin, flavopiridol and suramin, as well as combinations and pharmaceutically acceptable salts, esters and other derivatives of the same.

In some embodiments of the invention, antioxidants may be used as therapeutic agents in neurostimulation systems, among other devices. Antioxidants may be employed, for example, to mitigate the effects of free radical formation after trauma or injury, including surgical trauma, among other effects. Examples of antioxidants include phenolic antioxidants (i.e., antioxidants containing a six sided aromatic ring, which as defined herein can be part of a multi-cyclic ring system, having a pendent alcohol group), including hindered phenols and polyphenolic antioxidants, such as butylated hydroxyanisole (BHA), butylated hydroxytoluene (BHT), and probucol; hydroquinones such as methyl hydroquinone, tertiary-butyl hydroquinone (TBHQ) and 1-O-hexyl-2,3,5-trimethyl hydroquinone (HTHQ); nordihydroguaiaretic acid (NDGA); alkoxyphenols such as 4-tert-butoxyphenol, 4-ethoxyphenol, 3-methoxyphenol and 2-tert-butyl-4-methoxyphenol; 2,2-methylene-bis-(4-methyl-6-tert-butylphenol); tocopherols such as alpha-tocopherol (vitamin E), beta-tocopherol, gamma-tocopherol and delta-tocopherol; phenolic acids and their esters including para-coumaric acid, caffeic acid, chlorogenic acid, ferulic acid, protocatechuic acid, cinnamic acid, gallic acid, alkyl gallates (e.g., propyl, octyl, dodecyl), and para-hydroxybenzoic acid, among others, as well as combinations and pharmaceutically acceptable salts, esters and other derivatives of the same. Other antioxidants include flavonoids, which are generally phenolic compounds, such as catechins, leucoanthocyanidins, flavanones, flavanins, flavones, anthocyanins, flavonols, flavones, isoflavones, proanthocyanidins, flavonoid, pyrocatechol derivatives, and so forth. Specific examples are catechin, quercetin and rutin. Further antioxidants include glutathione and ascorbic acid (vitamin C), as well as its salts (e.g., sodium and calcium ascorbate) and its esters (e.g., ascorbyl palmitate and ascorbyl stearate).

Combinations of two or more therapeutic agents may be used, for example, selected from two or more of the foregoing agents. For instance, a steroid such as dexamethasone (DEX) may be delivered to the patient, along with an antiproliferative/antineoplastic agent such as paclitaxel or everolimus, among many other possible combinations.

As previously indicated, therapeutic agents such as those above may be provided in combination with a suitable polymeric material. In addition to providing a therapeutic agent carrier function, such polymeric materials may be selected to provide desired mechanical, electrical and/or chemical properties. Thus, polymeric materials may be used in varying capacities in the devices of the invention, including use as drug release coatings and use in forming various device components. For instance, in neurostimulation systems, therapeutic-agent containing polymeric materials may correspond to lead body materials, to insulating layers for lead extensions or to casing materials for neurostimulators such as IPGs, among many other possibilities. Examples of polymeric materials for use in forming such components may be selected from the polymers listed above and include silicones, polyurethanes, and block copolymers, among many others.

In certain embodiments, a polymeric material is selected which also provides a desired therapeutic function. Examples of such polymeric materials include those containing therapeutic polymers such as antioxidant polymers. Such polymeric materials may also contain additional polymers other than therapeutic polymers (e.g., to provide desired mechanical, electrical and/or chemical properties, etc.), which may be selected from those polymer described elsewhere herein. Thus, in some embodiments, the therapeutic polymer may be used as the sole polymer within a polymeric material (e.g., polymeric material used in forming a device, device component or device coating), whereas in other embodiments, one or more additional polymers may be included.

Specific examples of antioxidant polymers include homopolymers and copolymers of hydroxystyrene and its derivatives, including 2-4-dicumyl 3-hydroxy styrene, among others.

Further specific examples of antioxidant polymers include block copolymers with one or more polymer blocks having antioxidant properties and one or more additional blocks, which may be, for example, selected from the various high Tg blocks, low Tg blocks, hydrophilic blocks and hydrophobic blocks described herein, among many others. For example, hydroxystyrene-containing blocks may constitute A blocks and the additional polymer blocks may constitute B blocks in block copolymer structures such as those described above.

For instance, such block copolymers may contain one or more homopolymer or copolymer blocks comprising hydroxystyrene and one or more hydrophobic homopolymer or copolymer blocks containing one or more of the following monomers: olefins such as ethylene, propylene and isobutylene, fluorinated monomers such as vinylidene fluoride, trifluoroethylene, chlorotrifluoroethylene, tetrafluoroethylene, hexafluoropropene, fluorinated vinyl ether and perfluoromethyl vinyl ether, higher alkyl acrylates and methacrylates such as n-butyl acrylate and lauryl acrylate, polyvinyl aromatics such as polystyrene, and siloxane monomers such as dimethylsiloxane, methylphenylsiloxane and diphenylsiloxane. A few specific examples of such polymers include poly(hydroxystyrene-b-isobutylene-b-hydroxystyrene), poly(hydroxystyrene-b-n-butyl acrylate-b-hydroxystyrene), poly(hydroxystyrene-b-dimethylsiloxane-b-hydroxystyrene), among many others.

As another example, polymers such as those listed elsewhere herein (including the various block copolymers described in the preceding section, such as those comprising A blocks and B blocks) may be provided with one or more additional polymer blocks having antioxidant properties. For instance, the polymer blocks having antioxidant properties may be provided at the ends or along the backbone of polymers listed elsewhere herein, among other possibilities. In a specific embodiment, the block copolymer is a CBABC or a CABAC pentablock copolymer, where the A and B blocks can be selected from those described above, and the C blocks represent hydroxystyrene-containing blocks. A few specific examples of such polymers include poly(hydroxystyrene-b-methyl methacrylate-b-n-butyl acrylate-b-methyl methacrylate-b-hydroxystyrene), poly(hydroxystyrene-b-methyl methacrylate-b-isobutylene-b-methyl methacrylate-b-hydroxystyrene), poly(hydroxystyrene-b-methyl methacrylate-b-dimethylsiloxane-b-methyl methacrylate-b-hydroxystyrene), poly(hydroxystyrene-b-styrene-b-isobutylene-b-styrene-b-hydroxystyrene), poly(hydroxystyrene-b-styrene-b-n-butyl acrylate-b-styrene-b-hydroxystyrene), and poly(hydroxystyrene-b-styrene-b-dimethylsiloxane-b-styrene-b-hydroxystyrene), among many others.

Modulation of Therapeutic Agent Release

Where a therapeutic agent is released from a medical device in accordance with the invention, release may be modulated using various techniques.

For example, in some embodiments, agent release may be modulated by changing the amount of therapeutic agent loading within a given polymeric material. In general, higher loading levels lead to higher release rates.

In some embodiments, agent release may be modulated by changing the form of the therapeutic agent within the device. For example, acidic therapeutic agents may be used in acidic form or in a salt form (e.g., those based on alkali/alkaline earth metals and amines, including amino acids, for instance, sodium, potassium, calcium, magnesium, zinc, triethylamine, ethanolamine, triethanolamine, meglumine, ethylene diamine, choline, arginine, lysine and histidine salt forms, among others). As another example, basic therapeutic agents may be used in basic form or in salt form (e.g., hydrochloride, hydrobromide, sulfate, nitrate, phosphate, mesylate, tosylate, acetate, propionate, maleate, benzoate, salicylate, fumarate, glutamate, aspartate, citrate, lactate, succinate, tartrate, hexanoate, octanoate, decanoate, oleate and stearate salt forms, among others).

In some embodiments, agent release may be modulated by applying a barrier layer over a therapeutic-agent-containing material to regulate release. Examples of materials for barrier layers include biostable and biodegradable polymers, which may be selected from those polymers described elsewhere herein, among others. Drug diffusion through the barrier layer may be controlled by material selection (e.g., the type of polymer or polymers forming the barrier layer, the molecular weight of the same, etc.), by varying the barrier layer thickness, or by providing pores in the barrier layer, among other methods. Where a biodegradable barrier layer is employed, therapeutic agent release may be controlled by selecting biodegradable materials with differing biodegradation rates. In these embodiments, surface degrading layers may be employed to minimize polymeric debris.

In certain embodiments of the invention, pores are created in a polymeric material (e.g., a device, device component, device coating, etc.) and the pores are filled with a composition that includes a therapeutic agent, with or without an additional material, such as a polymeric or non-polymeric matrix material. Therapeutic agent release may be controlled in these embodiments, for example, by modifying depth, width and number of the pores or by modifying the type and relative amount of the matrix material, if any.

Pores may be created in a polymeric material, for example, using laser ablation. Various lasers are available for laser ablation. For example, excimer lasers are a family of pulsed lasers that are capable of operating in the ultraviolet region of the spectrum. Laser emission is typically generated in these lasers using a gas such as a halogen-based gas (e.g., fluorine, chlorine, hydrogen chloride, etc.) and/or a noble gas (e.g., krypton, argon, xenon, etc.). The particular gas or gas combination employed determines the output wavelength. Available excimer lasers include $F_2$ (157 nm wavelength), ArF (193 nm), KrCl (222 nm), KrF (248 nm), XeCl (308 nm), and XeF (351 nm) lasers. The average power for these lasers is commonly in the range of 10 W to 1 kW, and the pulse length may be, for example, in the 10-20 ns range, among other possibilities. Bulk mass removal, even from fine excavations such as 1 micron holes, has been demonstrated using such lasers.

Figure 5:
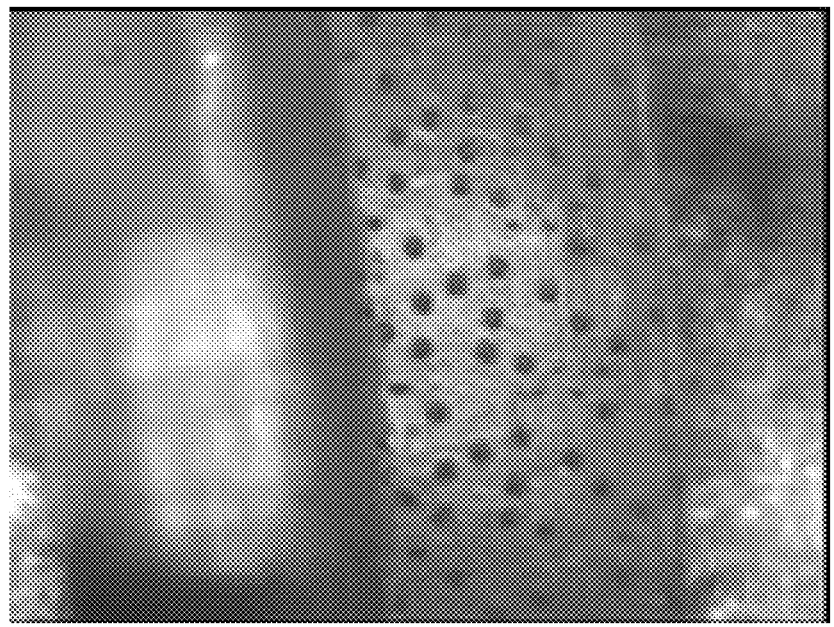
FIG. 5 is an optical image of an excimer-laser-ablated silicone material which has a pattern of 25-30 µm diameter pores.

The pores may be of various geometries and sizes (but are typically less than 50 μm (microns) in diameter, for example, ranging from 50 μm to 25 μm to 10 μm to 5 μm or less). Arrays of pores may be in any pattern (e.g., hexagonal, etc.). FIG. 5 is an optical image of a silicone material which has been ablated by an excimer laser to form a pattern of 25-30 μm diameter pores. Another method of creating pores in polymeric material is through the use of molds which have protrusions that would create pores or other depressions during the molding process.

In embodiments where a therapeutic agent is released from a polymeric carrier, release may be modulated, for example, based on the type of matrix material or the amount of matrix material relative to the therapeutic agent, among other possibilities.

For example, where a biodegradable matrix material is employed, therapeutic agent release may be controlled by selecting biodegradable matrix materials with differing biodegradation rates. In these embodiments, surface degrading polymers such as polyanhydrides and polyorthoesters may be employed to minimize polymeric debris.

As another example, the hydrophilic/hydrophobic balance of the polymeric carrier may be changed to modulate release.

For example, in the case of a hydrophilic polymer, the polymer may be modified by attaching hydrophobic polymer blocks to one or more ends of the polymer. Hydrophobic blocks may be selected from those described above among others. Conversely, in the case of a hydrophobic polymer such as SIBS, the polymer may be modified by attaching hydrophilic polymer blocks to one or more ends of the polymer. Hydrophilic blocks may be selected from those described above among others.

As another example, in the case of a hydrophilic polymer, the polymer may be blended with one or more hydrophobic polymers, which may be selected from those described above, among others. Conversely, in the case of a hydrophobic polymer, the polymer may be blended with one or more hydrophilic polymers, which may be selected from those described above, among others. For instance, in one particular embodiment, a hydrophobic polymer such as SIBS is blended with a more hydrophilic polymer, for example, a maleic anhydride homopolymer or a maleic anhydride copolymer such as poly (styrene-co-maleic anhydride) (SMA). In this regard, previous work with stent coatings has shown tunable paclitaxel release using SMA/SIBS blends as polymeric carriers. See, e.g., Pub. No. US 2003/0235602 to Schwarz. The rate of drug release is a function of the wt % of SMA incorporated into the polymer coating blend. In a particular embodiment, chelation between certain therapeutic agents (e.g. DEX) and the maleic anhydride units within the maleic anhydride homopolymer or copolymer (e.g., SMA) may take place. This in turn may allow for control over drug release by varying the ratio of maleic anhydride polymer to DEX in the coating and/or by varying the maleic anhydride content within a given maleic anhydride copolymer. In other embodiments, a maleic anhydride homopolymer or copolymer may be used as the sole carrier material for the therapeutic agent.

Processing

As noted above, in various embodiments of the invention, polymeric materials are provided for use in forming all or a portion of implantable or insertable medical devices, including neurostimulation devices, among others. Such polymeric materials may correspond, for example, a device, device component, or device coating, and may be formed using various techniques.

For example, where the polymeric material contains one or more polymers having thermoplastic characteristics, a variety of thermoplastic processing techniques may be used. For instance, a method may be used that comprises the following: (a) providing a melt that contains one or more polymers as well as any other desired species (so long as they are stable under processing conditions) such as one or more therapeutic agents and (b) subsequently cooling the melt. Examples of thermoplastic processing techniques include the following, among others: injection molding, blow molding, compression molding, spraying, vacuum forming and calendaring, extrusion into sheets, fibers, rods, tubes and other cross-sectional profiles of various lengths, and combinations of these processes.

Other processing techniques besides thermoplastic processing techniques may also be used, including solvent-based techniques. For instance, a method may be used that comprises the following: (a) providing a solution or dispersion that contains a solvent, one or more polymers, and any other desired species such as one or more therapeutic agents, and (b) subsequently removing the solvent. The solvent that is ultimately selected will contain one or more solvent species, which are generally selected based on their ability to dissolve or disperse the polymer(s) and any other desired species. Examples of solvent-based techniques include the following, among others: solvent casting techniques, spin coating techniques, web coating techniques, spraying techniques, dipping techniques, electrostatic techniques, direct deposit techniques such as ink jet techniques, and combinations of these processes.

In some embodiments of the invention, a solution or dispersion (where solvent-based processing is employed) or a melt (where thermoplastic processing is employed) is applied to a substrate. For example, the substrate can correspond to all or a portion of a medical device to which a polymeric coating is applied, for example, by spraying, dipping, extrusion, and so forth. The substrate can also be, for example, a template, such as a mold, from which the polymeric material is removed after solidification. In other embodiments, for example, co-extrusion techniques, polymeric materials may be formed without the aid of a substrate.

In some embodiments, one or more therapeutic agents may be provided within a polymeric material at the time of formation, for instance, by including the therapeutic agent(s) in a polymer melt, solution or dispersion that is used to form the polymeric material. Therapeutic agent(s) may also be provided on or within a polymeric material after the polymeric material is formed (e.g., by exposing the polymeric material to a solution that contains the therapeutic agent(s)).

In certain embodiments, an implantable lead, adapted for insertion into a cochlea, may be formed using a modification of a method described in U.S. Pat. No. 6,862,805 to Kuzma et al., which includes the following: forming electrical contact pieces made from a precious, biocompatible material (e.g., platinum) into a desired shape; attaching the electrical contact pieces to a foil sheet made from a chemically-active metal (e.g., iron); connecting a wiring system to the metal contact pieces; molding a flexible lead body around the electrical contact pieces and wiring system while such are held in place by the foil sheet; and etching away the foil sheet, leaving the electrical contact pieces exposed at a surface of the molded lead body.

Figure 3A:
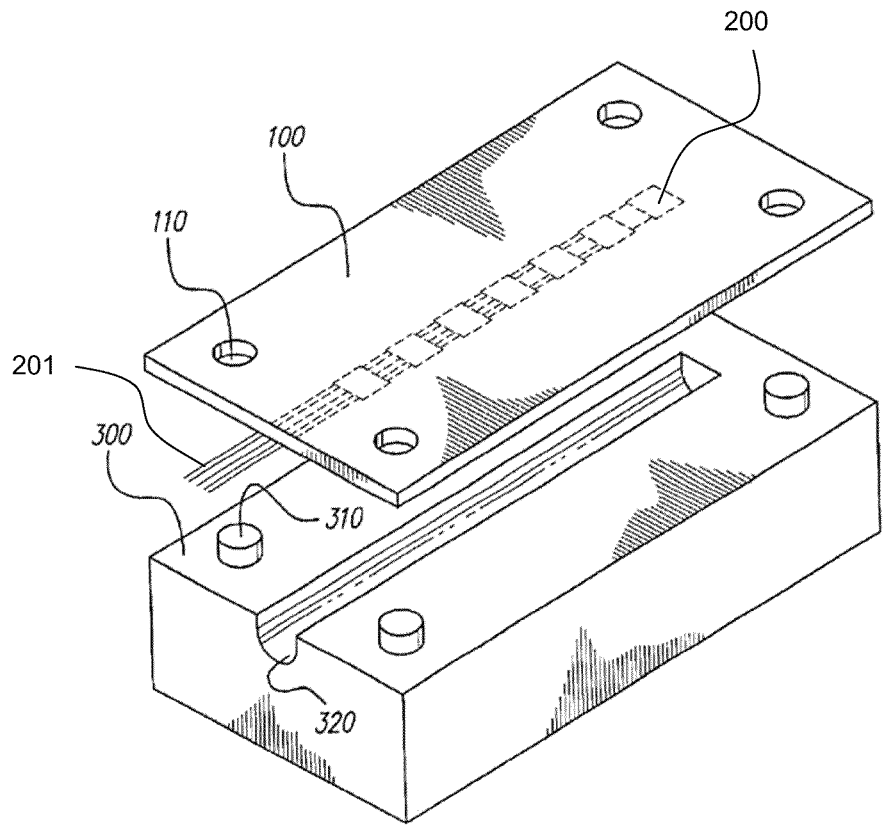
FIG. 3A is a schematic perspective view of a lead pre-assembly and mold for forming a cochlear lead in accordance with the prior art.
Figure 3B:
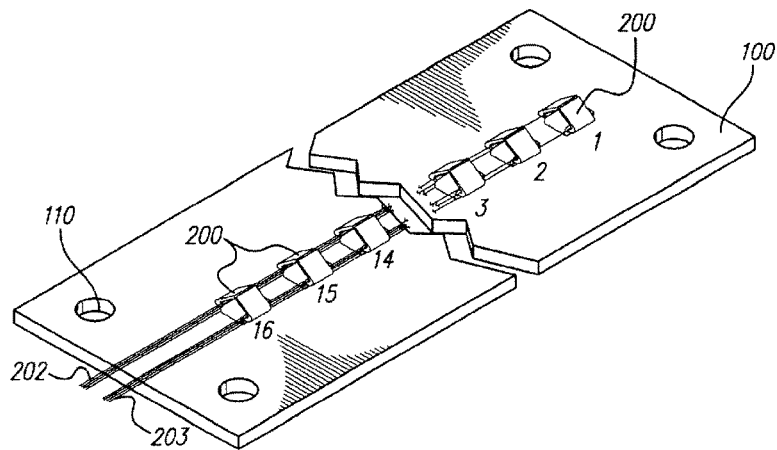
FIG. 3B is a schematic perspective view of a lead pre-assembly similar to that of FIG. 3A in accordance with the prior art.

With reference to FIG. 3A, the molding and subsequent process steps are described in more detail. FIG. 3A depicts a lead pre-assembly including an iron foil sheet 100 with alignment holes 110 and seven attached electrical contacts 200, to each of which is attached an interconnecting wire 201. (Shown in FIG. 3B is the obverse side of an lead pre-assembly similar to that shown in FIG. 3A, which includes a foil sheet 100, alignment holes 110, and sixteen electrical contacts 200, having interconnecting wires formed into wired bundles 202, 203.) Referring back to FIG. 3A, also shown is a mold 300, which includes alignment pegs 310 adapted to align with corresponding alignment holes 110 in the foil sheet 100. The mold 300 further has a channel 320 formed therein. Upon engagement of the lead pre-assembly with the mold 300 (by inserting alignment pegs 310 into alignment holes 110) a mold assembly with a cavity is created into which an amount of polymeric material (e.g., uncured silicone rubber) required to form the lead body is injected. This cavity or channel 320 may be shaped as desired. For example, the mold 300 depicted in FIG. 3A would form a linear lead body, however, another mold design is described in U.S. Pat. No. 6,862,805 which forms curved lead bodies. After the polymeric material solidifies, the foil carrier 100 (along with associated contacts 200, interconnect wires 201, and cured silicone) is removed from the channel 320 of the mold 300. The foil carrier 100 is exposed to a mixture of diluted acids (HNO$_3$ and HCl), which dissolves the foil carrier 100, thereby exposing a clean surface of the electrical contacts 200. For further details, see U.S. Pat. No. 6,862,805.

Silicone rubber (crosslinked polydimethylsiloxane), also commonly referred to as "silicone", is a common elastomer used in the manufacture of medical devices including cochlear implants, catheters and gastric balloons, among others. The polydimethylsiloxane (PDMS) is chemically crosslinked (cured) to impart elastomeric properties. This processing is hostile to therapeutic agents that may be dispersed in the PDMS at the time of crosslinking and moreover makes it difficult to load the silicone rubber with a therapeutic agent after its formation (e.g., by penetration with a solvent).

Various block copolymers, on the other hand, have elastomeric properties required for lead bodies and other device applications, but do not require the use of chemical crosslinking steps. Such block copolymers also allow for the modulation of drug delivery rates based on the composition and relative amounts (e.g., relative molecular weights) of the individual blocks used (as well as other factors, including drug loading, the use of additives, etc.).

Thus, in some embodiments of the invention, leads for neurostimulation devices and other similar devices are formed using biocompatible block copolymers, which may be, for example, selected from those described above (e.g. SIBS, MBAM, etc.), among others. Methods for manufacturing such devices include methods based on solutions and melts of such copolymers (which may also optionally contain additional agents, such as therapeutic agents and release modifying agents, among others), as described above. The elastomeric properties of the material can be customized (e.g., based on the composition and relative amounts of the individual blocks within the copolymers, etc.) to suit mechanical properties of the application at hand.

For example, in accordance with an embodiment of the invention, a block copolymer is provided in the form of a solution or a melt, along with any additional agents (e.g., therapeutic agents, etc.) and injected into a mold cavity with associated contacts and interconnection wires (e.g., using an assembly like that of FIG. 3A, among numerous other possibilities). After the solution or melt has solidified, the resulting assembly may be processed to form a lead with a polymeric lead body, exposed contacts and embedded interconnection wires. In certain of these embodiments, the finished product contains a therapeutic agent, which may be eluted from the device upon implantation, without the need for an additional coating process.

In one specific embodiment, a solution of SIBS and DEX in an organic solvent, such as THF, toluene, chloroform, or a mixture thereof, may be injected into a mold cavity and the solvent subsequently removed. In another specific embodiment, a melt of SIBS and DEX may be injected into a mold cavity and cooled. Where the volume shrinks substantially upon solvent evaporation or cooling, the mold may be filled multiple times.

In accordance other embodiments of the invention, a therapeutic agent (which may further include a polymeric material carrier) may be deposited on a contact, or on an interconnection wire, or on a mold surface (e.g., using an assembly like that of FIG. 3A, among numerous other possibilities). A liquid composition (e.g., a melt, solution, dispersion, curable composition, etc.) containing a polymer (e.g., silicone, a block copolymer, or another polymer), along with any desired additional agent (e.g., therapeutic agent, etc.), is then injected into the mold cavity. After the polymer composition has solidified (e.g., due to cooling, solvent removal, cure, etc.), the resulting assembly may be processed to form a lead with a polymeric lead body portion, exposed contacts and embedded interconnection wires.

Figure 4:
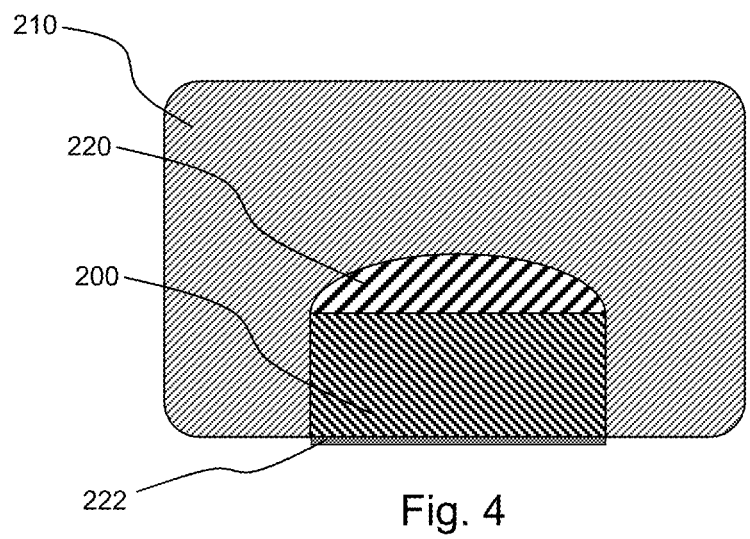
FIG. 4 is a schematic cross-sectional illustration of a lead in accordance with an embodiment of the invention that includes a contact, a therapeutic agent and lead body.

For example, with reference to FIG. 4, a therapeutic agent 220 may be deposited on the back side of a contact 200 prior to forming a polymeric lead body 210, which lead body 210 partially surrounds the contact 200 and completely encases the therapeutic agent 220. Upon implantation into a subject, the therapeutic agent may migrate through the polymeric material of the lead body 220 and/or along the interface between the contact 200 and the polymeric material of the lead body 210 and elute into the subject. If desired, the same or a different therapeutic agent can be optionally disposed at the surface of the device for burst release (e.g., in the form of a coating 222), for example, to supplement the delayed release from the agent behind the contacts.

As indicated above, therapeutic agents may also be provided on or within a polymeric material (e.g., device, device component, coating, etc.) after the polymeric material has been formed.

For example, a polymeric material (e.g., one formed from a block copolymer, etc.) may be contacted with a solution that contains a therapeutic agent (e.g., by dipping, spraying, or other application technique). The solvent for the therapeutic agent may be selected based on its ability to dissolve the therapeutic agent as well as its ability to swell or partially dissolve the polymer(s) making up the polymeric material. As a specific example, a solution of a therapeutic agent such as DEX in an organic solvent such as THF, toluene, chloroform or a mixture thereof, may be sprayed or otherwise applied to a polymeric material that contains or consists of SIBS.

In certain embodiments, SIBS is mixed with silicone, swelled, and then impregnated with any of a variety of biostable polymers such as those described elsewhere herein. Drugs such as dexamethasone, among many others, can also be impregnated into the SIBS/silicone mixture. Therapeutic uptake may be enhanced in some embodiments by employing reduced molecular weight polymer within the polymeric material. Without wishing to be bound by theory, it is believed that reduced molecular weight polymers have loosely bound chain entanglements with lower intermolecular forces that allow for therapeutic agent to more readily penetrate through the polymer matrix, relative to higher molecular weight material. SIBS with a molecular weight ranging from 1 kDaltons or less to 2.5 kDaltons to 5.0 kDaltons to 10 kDaltons to 25 kDaltons to 30 kDaltons is a specific a example of a lower molecular weight polymer, whereas SIBS with a molecular weight ranging from 30 kDaltons to 50 kDaltons to 100 kDaltons to 200 kDaltons or more is a specific a example of a higher molecular weight polymer. Typically, the styrene content of the SIBS ranges from 10 mol % or less to 15 mol % to 17 mol % to 20 mol % to 25 mol % to 30 mol % to 40 mol % or more.

As another example, a layer of material comprising a therapeutic agent, either with or without an additional material (e.g., a polymer matrix, etc.), may be applied to a previously formed polymeric material after the polymeric material has been formed.

In some embodiments, a therapeutic agent and a non-polymeric matrix material may be applied to a previously formed polymeric material. For example, a mono-, di- and/or tri-glyceride coating may be employed for rapid drug release. One example of such a non-polymeric matrix material is CISCOAT an oil-based cis-hydrogenated coating that has the capacity for high drug loadings that are tunable. More particularly, such coatings comprise cis-hydrogenated fatty acids and/or fatty acid esters (e.g., coatings comprising from 5% or less to 10% to 20% to 50% or more of one or more of such species), for example, selected from natural vegetable or animal fatty acids and fatty acid esters, such as omega-3-fatty acid from fish oil or cod liver oil, among many others. Cis-hydrogenated species include mono-, di- and tri-glycerides as well as esters thereof. In certain embodiments, the fatty acids and/or fatty acid esters are trans-free hydrogenated. Examples of such cis-hydrogenated species are set forth in WO 2005/053767 to De Scheerder et al.

In certain embodiments, the present invention provides methods for coating neurostimulation leads, including cochlear leads, SCS leads and DBS leads, among others, using techniques that allow for coating of specific surfaces of the leads (e.g., polymeric surfaces) while avoiding applying coating material other surfaces of the leads (e.g., electrical contacts). The coating may be, for example, a barrier coating containing one or more polymers, or a therapeutic-agent-releasing coating containing one or more polymers and one or more therapeutic agents, among other possibilities. The coating may be applied, for example, as a solution, dispersion, melt or curable composition.

A first method of selectively applying a coating to a neurostimulation lead is by direct deposit. Direct deposit techniques include "direct write" technology, which works similar to an ordinary pen. Direct deposit can be, for example, by a modified DNA pen, or by a micro-spotting pen, such as that manufactured by TeleChem International and described in U.S. Pat. No. 6,101,946. Other methods include mask-based and maskless deposition, for example, maskless mesoscale material deposition (so-called "$M^3D$"), such as that by Optomec, Inc., Albuquerque, N. Mex., USA.

Figure 7B:
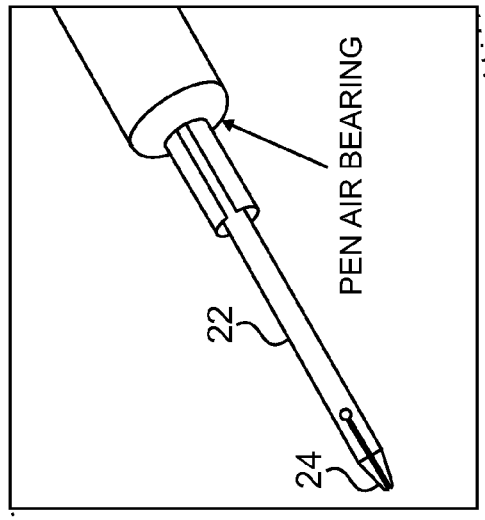
FIGS. 7A, 7B and 7C show three views of a microspotting pen for use in a direct deposit method in accordance with an embodiment of the present invention.
Figure 7C:
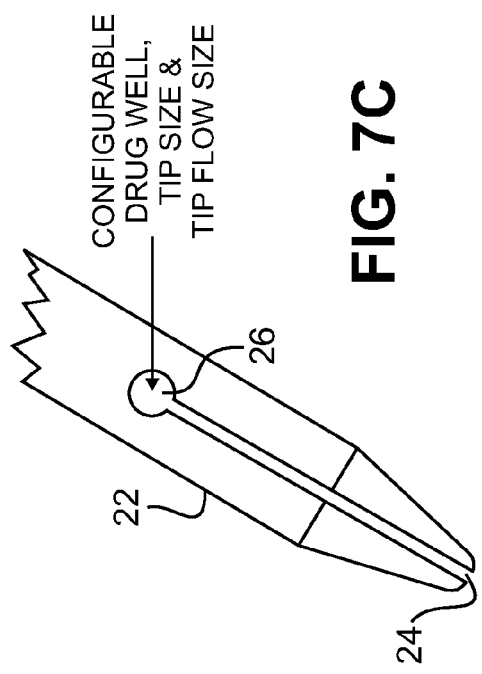
Figure 7A:
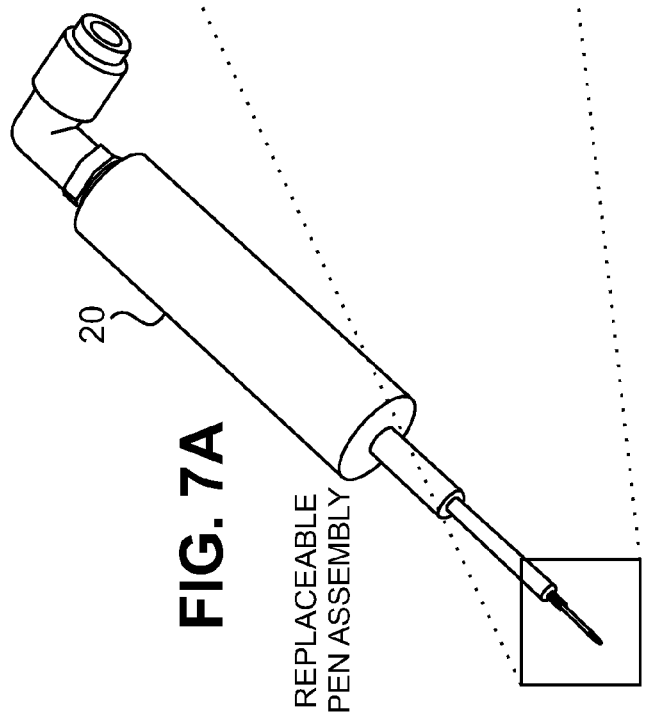

Turning now to FIG. 6, a direct deposit dispenser 2 is schematically shown, which can deposit a material 8 along a surface of a neurostimulation lead 4, for example, a surface having electrical contacts 6 or another surface of the lead (deposition along the surface opposite the contacts is illustrated). The dispenser 2 may be thin, for example, having a diameter of about 1 mm or less. The dispenser 2 may be held upright or at any angle in order to deposit material 8 with specificity. A specific example of a direct deposit dispenser is a micro-spotting pen 20 as shown in FIG. 7A. As shown in more detail in FIGS. 7B and 7C, the micro-spotting pen 20 has a split distal end 22 that is dipped into a solution reservoir (not shown) to load the pen 20. As the pen 20 is removed from the reservoir, a droplet is formed at the distal-most tip 24 of the pen. When the pen tip 24 contacts the surface of the lead 4, the surface tension causes the solution 8 to be drawn from the well 26 in the distal end 22. This technique allows for a continuous stream of solution 8 until the well 26 is emptied, when the pen 20 is re-dipped in the reservoir for further application.

A further method of applying a coating to a neurostimulation lead is via a drop-on-demand inkjet, as shown schematically in FIG. 8. This technique works similar to that of an inkjet printer for paper. The inkjet nozzle 30 dispenses droplets of material 8 along a surface of a neurostimulation lead 4, for example, a surface having electrical contacts 6 or another surface of the lead (deposition along the surface opposite the contacts is illustrated). The inkjet nozzle 30 is controlled by a piezoelectric actuator or a thermal bubble actuator (not shown), which can control the time of ejection and the size and speed of the dispensed droplets for precision material placement. The peripheral tooling of the device may be such that imaging allows the user to accurately line up the nozzle 30 with the lead 4.

Further methods of coating neurostimulation leads are based on covering the electrical contacts before coating the rest of the device. The electrical contacts may be covered with an easily removable substance, such as a polymer mask deposited by electrospray techniques or semiconductor masking tape. Once the electrical contacts have been covered, the entire device can then be coated using any available coating technique, such as dip coating, roll coating, spray coating, or direct deposit coating, among other methods. Once the coating process has been completed, the covering on the electrical contacts is removed. For instance, the polymer mask may be removed by laser ablation or solvent dissolution, or the semiconductor masking tape may be removed by using minimal mechanical force.

Medical Devices Based on Silicone and Additional Polymers, Including Block Copolymers As indicated previously, silicone, which is based on crosslinked PDMS, is a common elastomer used in the manufacture of medical devices. Typically, the PDMS is chemically crosslinked to impart elastomeric properties to the material. The crosslinking process, however, is hostile to therapeutic agents that may be present during processing and may make it difficult to load the silicone with a therapeutic agent after its formation. Silicone, however, has mechanical and electrical properties that make it otherwise ideal for use in forming various medical devices, including lead bodies for neurostimulation leads such as SCS leads, DBS leads, and cochlear leads, among others.

Because they form physical crosslinks, rather than chemical crosslinks, block copolymer materials (e.g., SIBS, etc.) can be formed under relatively gentle conditions (e.g., solvent-based formation methods) and they are relatively easy to load with therapeutic agent once formed (e.g., by contact with a therapeutic agent containing solution). Various block copolymer (e.g., SIBS, etc.) are also known to have enhanced biocompatibility.

Certain aspects of the invention take advantage of the beneficial properties of both silicone rubber and block copolymers. For example, in some embodiments, the invention provides neurostimulation leads, which comprise a lead body formed from silicone rubber and a block copolymer layer disposed over the silicone rubber, which may further optionally include a therapeutic agent. Such a block copolymer layer may, for example, improve biocompatibility and/or provide for drug release, among other functions.

A lead body may be formed from silicone rubber, for example, using a process like that described above, among many other possibilities. Once such a lead body is formed, in some embodiments, a solution, dispersion or melt of a polymer such as a block copolymer or another type of polymer (which may optionally contain a therapeutic agent) may be contacted with the lead using any of a variety of techniques. For instance, a solution of SIBS and, optionally, a therapeutic agent such as DEX, can be dissolved in an organic solvent, such as THF, toluene, chloroform or a mixture thereof, and applied to the silicone rubber portion of a neurostimulation lead. Application methods include those described above, such as dipping, spraying, roll coating, direct deposit, ink jet, mask based deposition, maskless deposition, modified DNA pen, micro-spotting pen, or another application technique.

Figure 9A:
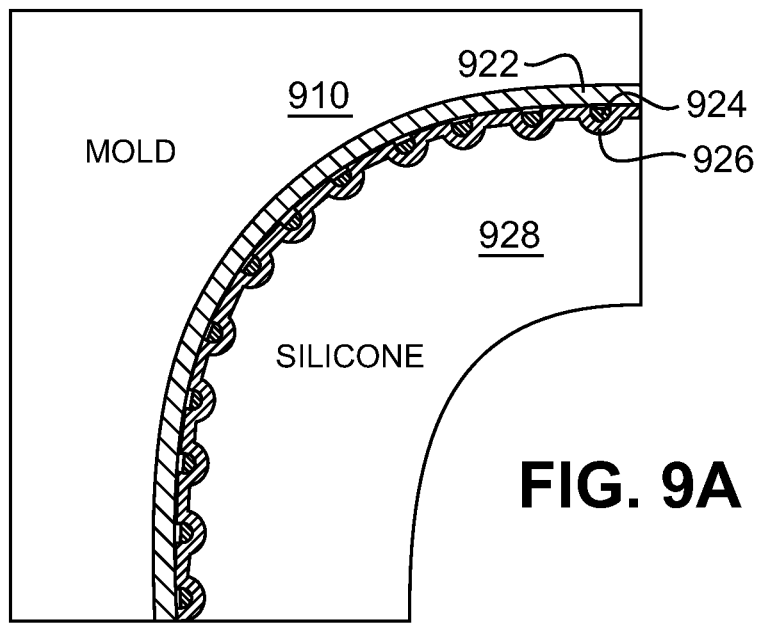
FIG. 9A is a schematic cross-section illustrating a molding technique for forming a neurostimulation lead, in accordance with an embodiment of the invention.
Figure 9B:
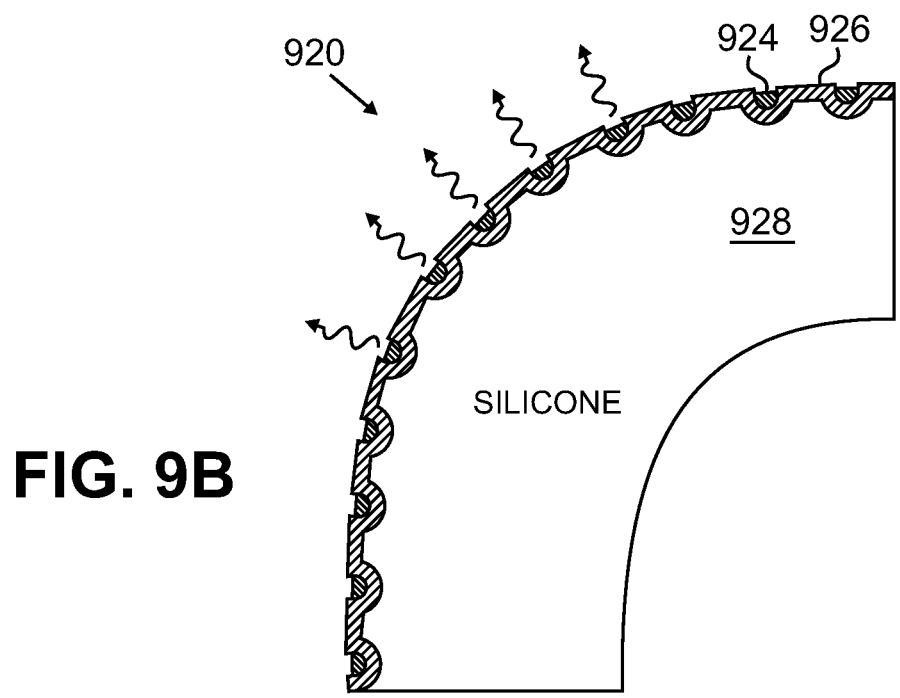
FIG. 9B is a schematic cross-section illustrating the neurostimulation lead of FIG. 9A, after being removed from the mold, in accordance with an embodiment of the invention.

In other embodiments, structures of this type are formed using mold-based techniques. For example, in one embodiment, and with reference to FIG. 9A, therapeutic agent particles 924 (e.g., DEX particles) are applied to a mold 910 (after first applying an optional mold release agent 922, as desired). The particles 924 are then encapsulated in a therapeutic agent binder 926, which may comprise, for instance, a polymer such as those described elsewhere herein (e.g., a block copolymer such as SIBS), among other possibilities. The particles may be encapsulated, for example, by applying a melt of a solution containing the therapeutic agent binder material to the therapeutic agent particles 924 on the mold 910. The mold 910 is then filled with a PDMS containing liquid, which is cured to form silicone rubber 928. When the resulting assembly 920 is released from the mold as shown in FIG. 9B (contacts and wiring are not illustrated in the cross-sections shown in FIGS. 9A-9B), the therapeutic agent particles 924 are partially encapsulated by the therapeutic agent binder 926. Consequently, the therapeutic agent is able to readily elute from the coating in vivo. The therapeutic agent binder may be optional in some embodiments, which would result in the therapeutic agent being partially encapsulated by the silicone (although the therapeutic agent would have to be able to withstand the silicone curing process).

In other embodiments (e.g., after first applying a mold release agent, as desired), the mold is lined, for example, with a layer polymer particles (e.g., spheres or other shapes) that contain a therapeutic agent (e.g., particles containing a therapeutic agent in a polymer matrix or particles in which a therapeutic agent is encapsulated by a polymer). The mold is then filled with a PDMS containing liquid, which is cured to form silicone rubber. In some embodiments, the polymer particles are encapsulated in a material that is not affected by acid etching (e.g., where acid etching is used to expose contacts as described above), followed by application of another material to remove the encapsulation medium after acid etching. Such materials include hydrophobic lipids as well as polymers that are crystalline and/or hydrophobic (e.g., polyamides, polyethylene, polypropylene, polystyrene, etc.), which materials are able to resist aqueous acids, but which may be subsequently dissolved in organic solvents.

In other embodiments (e.g., after first applying a mold release agent, as desired), the mold is lined, for example, with a therapeutic-agent-containing polymeric layer. For example, a polymeric layer comprising a mixture of therapeutic agent such as dexamethasone and a block copolymer such as SIBS may be applied to a mold in a liquid state (e.g., as a solution, dispersion or melt). After solidification of the therapeutic-agent-containing polymeric layer, the mold is then filled with a PDMS containing liquid, which is cured to form silicone rubber.

In certain of the preceding embodiments, an intermediate layer (also referred to herein as a "tie layer") may be provided between the outer polymer containing material and the inner silicone material, in order to enhance adhesion between the materials. Materials suitable for such layers are discussed in more detail below.

In certain of the preceding embodiments, selective application of the therapeutic-agent-containing layer to the mold or selective masking of the mold may be employed to control the location/distribution of the therapeutic agent on the device surface.

As noted above, silicone rubber is chemically crosslinked to impart elastomeric properties to the material. At least in part as a result of the cross-linking, silicone resists adhesion of various materials. Thus, in accordance with various embodiments of the invention, techniques and structures are provided which improve adhesion of materials (including polymeric materials containing polymers such as those described elsewhere herein, among others) to silicone surfaces. Such materials may be adhered to silicone, for example, to improve biocompatibility and/or to provide a drug release function, among other reasons. Increasing adhesion improves coating durability and/or encourages reproducible drug release profiles, among other advantages.

Various embodiments of the invention described herein are based on neurostimulation devices having a silicone lead body and a SIBS coating. SIBS is one example of a polymeric material that may be used as a biocompatible coating material for silicone in neurostimulation devices, including implantable stimulation leads. SIBS may also be used to regulate delivery of a therapeutic agent from such medical devices. However, a variety of other polymeric materials and non-polymeric coating materials may also be employed to serve the same purpose. Moreover, the ability to adhere materials to silicone is of use in a variety of medical devices other than neurostimulation devices.

In some embodiments of the invention, adhesion to a silicone rubber surface may be improved by modification of the silicone rubber (e.g., by physical treatment, chemical treatment, or both) before, during, or after the application of an additional layer.

Figure 10:
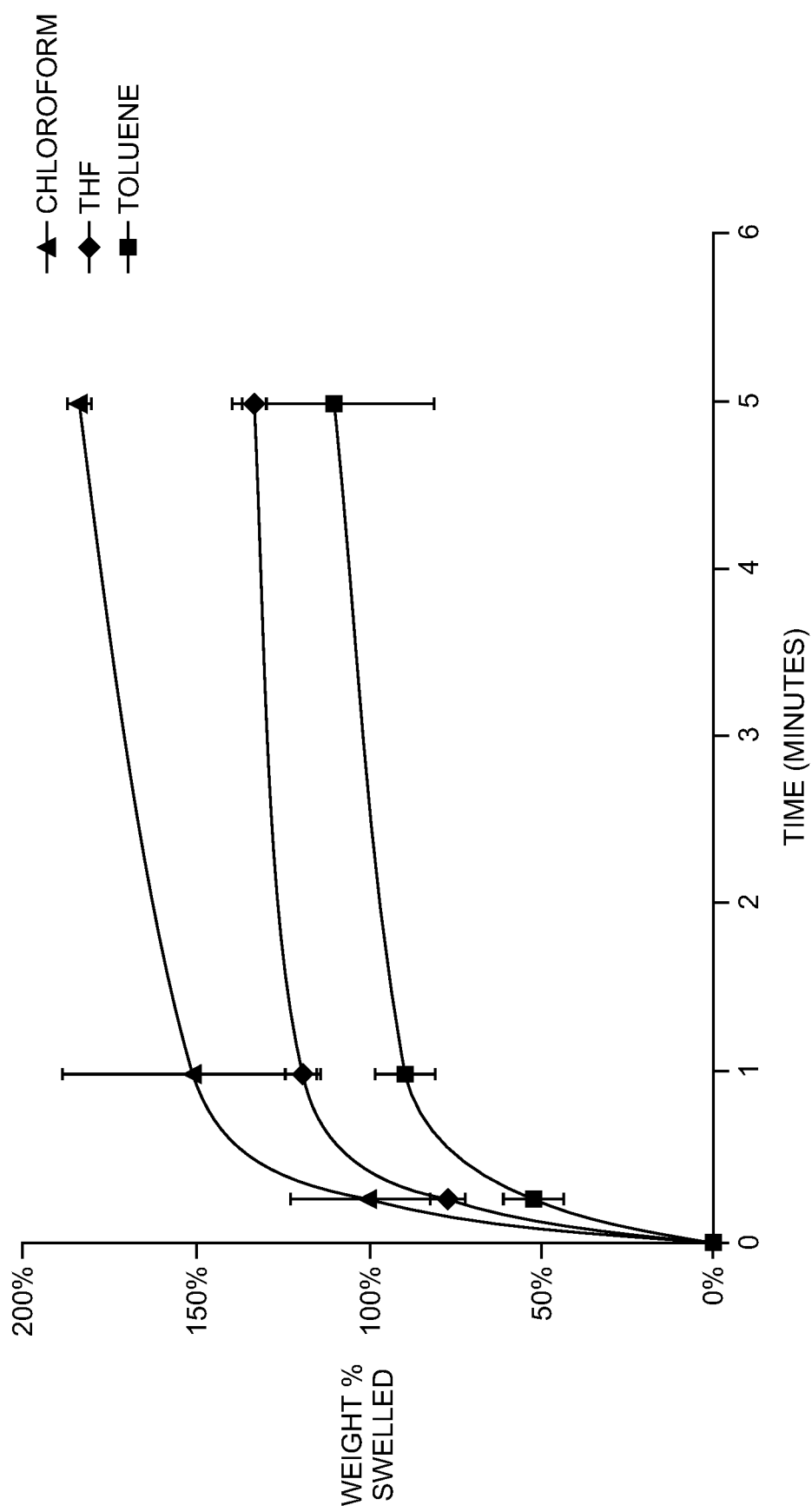
FIG. 10 is a plot of weight % gained for silicone samples after exposure to chloroform, tetrahydrofuran (THF), and toluene.

For example, in some embodiments of the invention, a silicone rubber surface may be modified by swelling the silicone rubber with a solvent, either before or during the application of an additional layer. The swelling of the silicone rubber allows for enhanced interpenetration between the silicone rubber and the subsequently added layer, thereby promoting adhesion. This may be achieved, for example, by soaking or spraying the silicone with a solvent prior to application of the additional layer. Additionally, a device may be coated with a solution containing a solvent and a coating material (e.g., SIBS in chloroform, THF or toluene, etc.), whereupon adhesion is promoted by ensuring that the time of exposure to the solvent (e.g., the time after solvent exposure and before solvent evaporation) is sufficient to induce sufficient swelling to improve adhesion. In this regard, various solvents including chloroform, THF and toluene have been shown to significantly swell the silicone portion of a cochlear implant in as few as 15 seconds (earliest time points tested). In this regard, FIG. 10 shows the weight percent change of silicone rubber test samples that have been immersed in various solvents as a function of immersion time.

In other embodiments, a silicone surface may be modified by texturing the surface of the silicone rubber to enhance mechanical interlocking between the silicone rubber and the subsequently applied layer of material.

For example, the silicone surface may be textured (e.g., roughened) by physical treatment, including scoring, scraping, and sand-blasting or grit-blasting using ceramic or other suitable media, among other techniques.

As another example, texturing (e.g., pores and other depressions) may be created using excimer laser ablation techniques such as those described above. Such techniques may increase wetting/spreading due to capillary effects associated with the formation of a textured surface. (Depending on the applied laser conditions, laser treatment may also be used to increase surface smoothness to increase the spreading and wetting of the coated layer, for example, where other steps have been taken to enhance adhesion. Wetting/spreading may be increased, for example, due to surface oxidation, including the formation of oxygen-containing groups such as hydroxyl groups.)

Texturing may also be created through the use of molds that impart textures directly on the device surface. For example, molds can be provided which have depressions and/or protrusions that would create inverse features (protrusions and/or depressions) in the silicone rubber during the molding process. Modification of a device mold may be made, for example, using standard chemical etching processes, among other possibilities. Such processes can produce small features (e.g. on the order of 2.5 μm). An advantage of this method is the elimination of post-cure processing steps to create surface textures on the device after fabrication.

Adhesion depends, for example, on various intermolecular forces, including covalent bonds and/or non-covalent interactions such as van der Waals forces, hydrophobic interactions and/or electrostatic interactions (e.g., charge-charge interactions, charge-dipole interactions, and dipole-dipole interactions, including hydrogen bonding). Thus, in some embodiments of the invention, adhesion to a silicone rubber surface may be improved by modification of the silicone rubber surface using chemical treatment.

For example, in some embodiments of the invention, the silicone surface may be subjected to a plasma treatment process. Plasma is the fourth state of matter and can be used to clean the silicone surface of organic contamination, to chemically modify the surface by imparting functional groups on the surface, or to polymerize one or more types of monomers on the surface, resulting in a polymeric material bound to the surface. The particular functional groups or polymeric material created are dictated by the plasma source gas(es) used. The particular functional groups or polymeric material created may be selected, for example, to have similar properties to that of the additional layer that is subsequently applied to the plasma treated silicone rubber surface.

As noted above, in some embodiments of the invention, adhesion to a silicone surface may be improved by modification of the silicone after an additional layer has been applied.

For example, because the high degree of cross-linking in silicone rubber ordinarily leads to decreased adhesion, in some embodiments of the invention, an additional layer is applied to a silicone surface which has been partially crosslinked. The partially crosslinked silicone rubber may be used in the final product. Alternatively, after the additional layer is deposited, the crosslinking level may be increased in the silicone, for example, through additional crosslinking.

In other embodiments, a crosslinkable polymer other than PDMS is initially introduced into the silicone during the device formation process. Subsequently, a layer of additional material, which also contains the crosslinkable polymer, is applied to the silicone-containing layer. For example, a layer containing a block copolymer (e.g., SIBS) and the crosslinkable polymer may be applied. The crosslinkable polymer is then crosslinked to form a therapeutic-agent-containing coating that is bound to the silicone rubber by an interpenetrating network.

In various embodiments of the invention, materials are provided which have enhanced adhesion to silicone rubber surfaces, including highly cross-linked silicone rubber surfaces.

For example, in some embodiments, a lower molecular weight polymer (e.g., SIBS having a molecular weight ranging from 1 kDaltons or less to 2.5 kDaltons to 5.0 kDaltons to 10 kDaltons to 25 kDaltons to 30 kDaltons or more) is substituted for a higher molecular weight polymer of the same type (e.g., SIBS having a molecular weight ranging from 30 kDaltons or less to 50 kDaltons to 100 kDaltons to 200 kDaltons or more) within the layer that is applied to the silicone. The lower molecular weight polymer is believed to allow for enhanced interpenetration into the underlying silicone, which may be enhanced, for example, by applying the lower molecular weight polymer to the silicone while dissolved in a solvent that swells the silicone. (Without wishing to be bound by theory, it is believed that the lower molecular weight polymer has shorter polymer chains with fewer and lower strength entanglements, which allow for better penetration into the silicone.)

In other embodiments, a lower molecular weight polymer is admixed with a higher molecular weight polymer of the same type and applied to the silicone.

In further embodiments, a layer comprising a lower molecular weight polymer is applied to the silicone, followed by a layer comprising a higher molecular weight polymer of the same type. In these embodiments, the layer of lower molecular weight polymer acts as a tie layer for the layer of higher molecular weight polymer.

In some embodiments of the invention, a material is applied to the silicone that contains a polymer that comprises one or more silicon-containing monomers such as siloxane monomers (e.g., one or more of dimethylsiloxane, diethylsiloxane, methylethylsiloxane, methylphenylsiloxane, etc.) to improve adhesion to the silicone. For example, in some embodiments, a polymer is selected that contains one or more polysiloxane blocks (e.g., PDMS blocks) and one or more additional polymer blocks.

For example, a polymer may be selected that contains one or more low Tg polysiloxane (e.g. PDMS, etc.) blocks and one or more high Tg blocks, which may be selected, for example from those set forth elsewhere herein. Examples of such polymers include block copolymers with low Tg polysiloxane A blocks and high Tg B blocks having structures such as those set forth above, for example, $(AB)_m$, $B(AB)_m$, $A(BA)_m$, $X(BA)_n$, and $X(AB)_n$, among others.

In other embodiments, polymers such at those previously described are modified with one or more polysiloxane blocks (e.g., PDMS blocks), for example, by providing the polymer with polysiloxane end blocks and/or polysiloxane side blocks. For example, the polymer may have A and B blocks, which can be arranged in one of the structures described above. As elsewhere herein, the composition of the A and B blocks may be chosen for their ability to provide specific properties to the device, including biocompatibility and mechanical properties, as well as drug release properties in some instances. In certain embodiments, the B block is selected to provide elastomeric properties, while the A blocks are selected to provide mechanical integrity (e.g., by providing physical crosslinks). The A and B blocks may also be independently selected to provide biocompatibility and/or controlled drug release. Many examples of A and B blocks are given elsewhere herein. A few specific examples of A blocks include high Tg homopolymer and copolymer blocks containing one or more of the following monomers: high Tg vinyl aromatics such as styrene, high Tg alkyl methacrylate monomers such as methyl methacrylate, ethyl methacrylate, isopropyl methacrylate, isobutyl methacrylate, t-butyl methacrylate and cyclohexyl methacrylate, high Tg acrylates such as isobornyl acrylate, as well as acrylonitrile, and vinyl pyrrolidone. A few specific examples of B blocks include low Tg homopolymer and copolymer blocks containing one or more of the following monomers: low Tg alkene monomers such as ethylene, propylene, isobutylene, and 1-butene, low Tg fluorinated monomers such as vinylidene fluoride and 2,2,2-trifluoroethyl acrylate, and low Tg alkyl acrylate monomers such as methyl acrylate, ethyl acrylate, propyl acrylate, isopropyl acrylate, n-butyl acrylate, sec-butyl acrylate, isobutyl acrylate and lauryl acrylate.

In certain embodiments, an A-B-A type block copolymer may be synthesized where the individual blocks contain functional groups capable of attaching polysiloxane blocks. The functional groups may be provided at the ends of the A blocks, along the length of the A blocks and/or along the length of the B blocks.

As a specific example, a PDMS-SIBS-PDMS block copolymer may be prepared by forming allyl groups at the polystyrene end blocks of SIBS, then attaching silicone hydride terminated PDMS to the SIBS by reaction via the allyl functional groups. For example, PDMS-SIBS-PDMS may be formed by the following technique: (a) chloromethyl groups are attached to the polystyrene end blocks of SIBS; (b) the chloromethyl groups are subsequently reacted with allyl magnesium bromide or allyl magnesium chloride to form allylated (carbon-carbon double bond) groups; and (c) silicone hydride terminated PDMS is attached to the SIBS by reaction with the allyl-functional groups to incorporate the PDMS grafts. In this regard, T. Higashihara et al., *Polymer Preprints,* 2007, 48(2), 1037, describe the formation of chloromethylated SIBS (using the method of S. Itsuno et al., *J. Am. Chem. Soc.* 1990, 112, 8187-88 in which poly(styrene-co-chloromethyl styrene) is formed by chloromethylation of a portion of the styrene monomers within linear polystyrene using trioxane and chloromethylsilane in the presence of stannic chloride), followed allylation of the chloromethylated SIBS using allyl magnesium chloride, and hydrosilation of the allyl-functionalized SIBS with silyl hydride functionalized poly(dimethyl siloxane).

In some embodiments, one or more additional polymers may be blended with the polysiloxane-containing polymer. Examples of such polymers may be selected from polymers described elsewhere herein. A few specific examples of polymers for use in conjunction with polysiloxane-modified SIBS can be selected from poly(styrene-co-maleic anhydride), SIBS, SEBS and PEG, among many others.

In some aspects of the invention, intermediate layers (also referred to herein as tie layers) are placed between a polymeric layer to be applied (e.g., SIBS, etc.) and silicone to improve the adhesion of the desired polymeric layer to the silicone. An effective tie layer provides good adhesion to both the silicone surface and the overlying polymeric layer, linking the two materials. As elsewhere herein, the overlying polymeric layer may contain a single type of polymer of may contain two or more types of polymer. The overlying polymeric layer may also optionally contain one or more therapeutic agents.

One class of tie layer already described is a low molecular weight version of a polymer in the overlying polymeric layer. The low molecular weight polymer may provide, for example, for enhanced interpenetration into swollen silicone, allowing it to function as a tie layer for a subsequently applied coating containing a higher molecular weight version of the polymer.

Another class of tie layer includes tie layers that contain at least one silicon-containing monomer and at least one monomer that is found in a polymer in the overlying layer (which may be referred to herein as a "common monomer"). For example, the tie layer may contain a polymer that contains (a) at least one polysiloxane block and (b) at least one block containing at least one monomer that is found in a polymer in the overlying layer (which may be referred to herein as a "common monomer block"). Examples of polysiloxane blocks include homopolymer and copolymer blocks having one or more of the following monomers, among others: dimethylsiloxane, diethylsiloxane, methylethylsiloxane, methylphenylsiloxane and diphenylsiloxane. Examples of such polymers include block copolymers with polysiloxane A blocks and common monomer B blocks, which have structures such as those set forth above (e.g., $(AB)_m$, $B(AB)_m$, $A(BA)_m$, $X(BA)_n$, $X(AB)_n$, etc.).

As specific examples, the following copolymers may be used as tie layers for SIBS among others: polysiloxane-modified SIBS such as that described above, polysiloxane-polystyrene copolymers including poly(styrene-b-dimethylsiloxane-b-styrene) and poly(styrene-b-dimethylsiloxane), polysiloxane-polyisobutylene copolymers including poly (isobutylene-b-dimethylsiloxane). Tie layers for MBAM include polysiloxane-polymethylmethacrylate copolymers, for example, poly(methyl methacrylate-b-dimethylsiloxane-b-methyl methacrylate) and poly(dimethylsiloxane-b-methyl methacrylate), among others. Poly(siloxane-butyl acrylate) copolymers may be employed as tie layers for MBAM, including poly(dimethylsiloxane-b-n-butyl acrylate). Many of the foregoing polymers are available from Polymer Source Inc., Montreal, Canada.

Additional examples of polymer tie layers include polysiloxane-polybutadiene block copolymers, phenyl siloxane, vinylsilane, silica anhydride in heptane, and SEBS modified with methyl methacrylate, among others.

Tie layers includes those tie layers that are formed using organosilicon compounds. Examples of organosilicon compounds include those of the formula $SiR^1{}_n R^2{}_{4-n}$ where n is an integer between 1 and 4. The $R^1$ groups in the preceding may be independently selected from alkoxy and alkanoyloxy groups, for example, straight chain or branched C1-C10 alkoxy and alkanoyloxy groups. Where crosslinking between the $R^1$ groups is desired, n is two, three or four. The $R^2$ groups may be independently selected from groups that contain one or more of the following: hydride, anhydride, azide, epoxy, ester, halogen, hydroxyl, isocyanate, phosphate and vinyl (including allyl) groups. In certain preferred embodiments, the $R^2$ groups are selected from hydride (—H) and C1 to C10 hydroxyalkyl groups.

Where n in the preceding compound formula is two or more (e.g., the compounds have two or more alkoxy and/or alkanoyloxy groups), the compounds can become crosslinked upon application to a silicone surface.

Where n in the preceding formula is four (e.g., tetraethoxysilane, tetraacetoxysilane, etc.), the crosslinked layer may form a non-covalent bond with the overlying polymeric layer.

Where n in the preceding formula is three or less, the crosslinked layer may contain reactive groups (e.g., hydride, anhydride, azide, epoxy, ester, halogen, hydroxyl, isocyanate, phosphate, vinyl, etc.) that are able to form covalent bonds with an overlying polymer layer. For example the overlying polymeric layer may contain a reactive polymer having one or more groups selected from the following among others: hydride, anhydride, azide, epoxy, ester, halogen, hydroxyl, isocyanate, phosphate and vinyl groups. Such functional groups may be found at the ends of the polymer or along the backbone(s) of one the polymer.

For example, an organosilane containing a hydride group may be used to form the crosslinked layer (e.g., an organosilane selected from triethoxysilane, triacetoxysilane, may be used, among others). The hydride group is reactive with an allyl functionality on a reactive polymer in an overlying layer. For instance, allyl functional SIBS may be formed from as described above. The allyl functional SIBS is then reacted with the silicon hydride groups in the underlying layer to form a covalent bond.

As elsewhere herein, the layer containing the reactive polymer may further contain one or more additional polymers. Examples include styrene maleic anhydride copolymers, SIBS, SEBS and PEG, among many others. The layer containing the reactive polymer may also optionally contain one or more therapeutic agents, such as dexamethasone, among many others.

Moreover, an additional layer may be provided over the layer containing the reactive polymer. For example, the reactive polymer may be selected to comprise at least one monomer that is found in an additional polymer in the overlying additional layer (i.e., a common monomer with regard to the additional polymer). As specific example, the organosilane compound may contain one or more silicon hydride groups and the reactive polymer may contain α,ω-dichloroallyl polyisobutylene are described in P. De et al., *Macromolecules* 2006, 39, 7527 or α,ω-dichloroallyl polystyrene or α,ω-dichloroallyl SIBS or allyl-functionalized SIBS as described in T. Higashihara et al. supra. A layer of SIBS (as the additional polymer) and an optional therapeutic agent such as dexamethasone may then be provided over the layer containing the reactive polymer.

Further, in other embodiments, a single layer may be formed which contains an organosilicon compound as described above, a reactive polymer as described above, one or more optional additional polymers, and one or more optional therapeutic agents. For example, the organosilicon compound may contain one or more silicon hydride groups, the functionalized polymer may contain an allyl group (e.g., α,ω-dichloroallyl polyisobutylene, α,ω-dichloroallyl polystyrene, α,ω-dichloroallyl SIBS, allyl-functionalized SIBS, etc.), the optional additional polymer may be SIBS, and the optional therapeutic agent may be dexamethasone.

In other embodiments of the invention, a tie layer is created by chemisorption of an organosilicon compound to a silicone surface. For instance, a silicone surface may be subjected to chemisorption of ethyleneoxy functionalized silanes, optionally after plasma treatment, for example, using argon as a processing gas. T. Aziz et al., *Journal of Dentistry* 2003, 31, 213-216.

In other embodiments, a tie layer is plasma polymerized on the silicone surface. The monomer(s) chosen to forming the tie layer may correspond to a monomer found in a polymer in a subsequently applied polymeric layer (i.e., a common monomer). In a particular embodiment, styrene groups can be plasma polymerized at the silicone surface, for example, after activation with oxygen or argon. This would produce a surface tailored to interact, for example, with the polystyrene blocks in SIBS.

In other embodiments of the invention, the silicone is treated by an ozonation process, followed by graft polymerization. See Y. Yuan et al., "Grafting sulfobetaine monomer onto silicone surface to improve haemocompatibility," *Polymer International* 2003, 53(1), 121-126.

Further enumerated aspects of the invention relating to the above are provided in the following paragraphs:

Aspect 1. An implantable neurostimulation lead comprising an electrical contact, an elongated conductor in electrical communication with the electrical contact and extending along at least a portion of the length of the lead, and a polymeric lead body comprising a block copolymer that supports the contact and encapsulates at least a portion of the length of the elongated conductor.

Aspect 2. The implantable neurostimulation lead of aspect 1, wherein the neurostimulation lead is selected from a spinal cord stimulation lead, a deep brain stimulation lead, and a cochlear lead.

Aspect 3. The implantable neurostimulation lead of aspect 1, wherein the block copolymer comprises a high Tg polymer block and a low Tg polymer block.

Aspect 4. The implantable neurostimulation lead of aspect 3, wherein the high Tg polymer block is a homopolymer or copolymer block comprising a monomer selected from high Tg vinyl aromatic monomers, high Tg alkyl methacrylate monomers, high Tg acrylate monomers, and combinations thereof and wherein the low Tg polymer block is a homopolymer or copolymer block comprising a monomer selected from low Tg alkene monomers, low Tg fluorinated monomers, low Tg alkyl acrylate monomers, low Tg siloxane monomers, and combinations thereof.

Aspect 5. The implantable neurostimulation lead of aspect 3, wherein the block copolymer comprises two high Tg polymer blocks separated by a low Tg polymer block.

Aspect 6. The implantable neurostimulation lead of aspect 1, wherein the molded polymeric lead body further comprises a therapeutic agent.

Aspect 7. The implantable neurostimulation lead of aspect 6, wherein the therapeutic agent is a corticosteroid.

Aspect 8. An implantable neurostimulation lead comprising an electrical contact, an elongated conductor in electrical communication with the electrical contact and extending along at least a portion of the length of the lead, and a polymeric lead body that supports the contact and encapsulates at least a portion of the length of the elongated conductor, wherein said neurostimulation lead comprises a block copolymer that comprises a polystyrene block and a polyisobutylene block and a therapeutic agent.

Aspect 9. The implantable neurostimulation lead of aspect 8, wherein the neurostimulation lead is selected from a spinal cord stimulation lead, a deep brain stimulation lead, and a cochlear lead.

Aspect 10. The implantable neurostimulation lead of aspect 9, wherein the block copolymer comprises two polystyrene blocks and a polyisobutylene block between the two polystyrene blocks.

Aspect 11. The implantable neurostimulation lead of aspect 8, wherein the block copolymer further comprises a hydrophilic block.

Aspect 12. The implantable neurostimulation lead of aspect 11, wherein the hydrophilic block is selected from homopolymer or copolymer blocks comprising monomers selected from carboxylic acid monomers and salts thereof, sulfonic acid monomers and salts thereof, vinyl pyrrolidone, vinyl alcohol, hydroxyethyl methacrylate, methyl methacrylate, hydroxystyrene, methyl vinyl ether, ethylene oxide, and combinations thereof.

Aspect 13. The implantable neurostimulation lead of aspect 8, wherein the block copolymer is blended with a maleic anhydride polymer.

Aspect 14. The implantable neurostimulation lead of aspect 15, wherein the maleic anhydride polymer is a styrene-maleic anhydride copolymer.

Aspect 15. The implantable neurostimulation lead of aspect 8, wherein the block copolymer is blended with a maleic anhydride polymer and dexamethasone.

Aspect 16. The implantable neurostimulation lead of aspect 8, wherein the polymeric lead body comprises the block copolymer.

Aspect 17. The implantable neurostimulation lead of aspect 16, wherein the lead body further comprises a therapeutic agent.

Aspect 18. The implantable neurostimulation lead of aspect 17, wherein the therapeutic agent is a corticosteroid.

Aspect 19. The implantable neurostimulation lead of aspect 8, wherein the lead body comprises silicone and wherein a layer that comprises the block copolymer is disposed over the silicone.

Aspect 20. The implantable neurostimulation lead of aspect 19, wherein the block copolymer further comprises a polysiloxane block.

Aspect 21. The implantable neurostimulation lead of aspect 19, wherein the layer comprises a low molecular weight poly(styrene-b-isobutylene-b-styrene) triblock copolymer, and further comprising a second layer over the first layer that comprises high molecular weight poly(styrene-b-isobutylene-b-styrene) triblock copolymer.

Aspect 22. The implantable neurostimulation lead of aspect 21 wherein the therapeutic agent is dexamethasone.

Aspect 23. The implantable neurostimulation lead of aspect 8, further comprising a barrier layer to regulate release of the therapeutic agent.

Aspect 24. The implantable neurostimulation lead of aspect 23 wherein the barrier layer is a porous barrier layer.

Aspect 25. The implantable neurostimulation lead of aspect 8, wherein the polymeric lead body comprises a plurality of depressions and wherein said therapeutic agent is disposed within said depressions.

Aspect 26. The implantable neurostimulation lead of aspect 25 wherein the depressions are laser-ablated pores.

Aspect 27. An implantable or insertable medical device comprising (a) a region comprising silicone and (b) a polymeric layer comprising a block copolymer disposed over the region.

Aspect 28. The medical device of aspect 27, wherein the medical device is an implantable neurostimulation device.

Aspect 29. The medical device of aspect 27, wherein the medical device is an implantable neurostimulation lead.

Aspect 30. The medical device of aspect 27, wherein the block copolymer comprises a high Tg polymer block and a low Tg polymer block.

Aspect 31. The medical device of aspect 30, wherein the high Tg polymer block is a homopolymer or copolymer block comprising a monomer selected from high Tg vinyl aromatic monomers, high Tg alkyl methacrylate monomers, high Tg acrylate monomers, and combinations thereof and wherein the low Tg polymer block is a homopolymer or copolymer block comprising a monomer selected from low Tg alkene monomers, low Tg fluorinated monomers, low Tg alkyl acrylate monomers, low Tg siloxane monomers, and combinations thereof.

Aspect 32. The medical device of aspect 27, wherein the block copolymer comprises a polystyrene block and a polyisobutylene block.

Aspect 33. The medical device of aspect 27, wherein the block copolymer comprises a polysiloxane block and a non-polysiloxane block.

Aspect 34. The medical device of aspect 27, wherein the block copolymer comprises (a) a polysiloxane block and (b) a polystyrene block or a polyisobutylene block or both a polystyrene block and a polyisobutylene block.

Aspect 35. The medical device of aspect 27, wherein the surface of the region is textured.

Aspect 36. The medical device of aspect 27, wherein the polymeric layer further comprises a therapeutic agent.

Aspect 37. The medical device of aspect 36, wherein the therapeutic agent is a corticosteroid.

Aspect 38. An implantable neurostimulation lead comprising an electrical contact, an elongated conductor in electrical communication with the electrical contact and extending along at least a portion of the length of the lead, a polymeric lead body, and an antioxidant.

Aspect 39. The implantable neurostimulation lead of aspect 38, wherein the antioxidant is released into a subject upon implantation into said subject.

Aspect 40. The implantable neurostimulation lead of aspect 38, wherein the antioxidant is an antioxidant polymer.

Aspect 41. The implantable neurostimulation lead of aspect 40, wherein the antioxidant polymer is a polymer that comprises hydroxystyrene.

Aspect 42. The implantable neurostimulation lead of aspect 38, wherein the polymeric lead body comprises said antioxidant.

Aspect 43. The implantable neurostimulation lead of aspect 38, further comprising a layer that is disposed over the polymeric lead body, wherein said layer comprises said antioxidant.

Aspect 44. An implantable neurostimulation lead comprising an electrical contact, an elongated conductor in electrical communication with the electrical contact and extending along at least a portion of the length of the lead, and a polymeric lead body, wherein said electrical contact has an external tissue contacting surface and an internal surface encased by the polymeric lead body, and wherein a layer comprising a therapeutic agent is disposed between the internal surface and the polymeric lead body.

Aspect 45. The implantable neurostimulation lead of aspect 44, wherein the therapeutic agent is a corticosteroid.

Aspect 46. The implantable neurostimulation lead of aspect 44, wherein the therapeutic agent is a dexamethasone.

Aspect 47. The implantable neurostimulation lead of aspect 44, comprising laser ablated pores in said polymeric lead body to facilitate drug release.

Aspect 48. A method of forming an implantable neurostimulation lead comprising an electrical contact, an elongated conductor in electrical communication with the electrical contact and extending along at least a portion of the length of the lead, and a polymeric lead body, said method comprising: providing a mold having a therapeutic-agent-containing layer comprising a therapeutic agent disposed over its surface; and molding the polymeric lead body within the mold.

Aspect 49. The method of aspect 48, wherein a release layer is provided between the mold and the therapeutic-agent-containing layer.

Aspect 50. The method of aspect 48, wherein the therapeutic-agent-containing layer further comprises a polymer.

Aspect 51. The method of aspect 50, wherein the polymer is blended with the therapeutic agent.

Aspect 52. The method of aspect 50, wherein the therapeutic-agent-containing layer comprises particles that comprise the polymer and the therapeutic agent.

Aspect 53. The method of aspect 52, wherein the particles comprise the therapeutic agent in a matrix that comprises the polymer.

Aspect 54. The method of aspect 53, wherein the particles comprise the therapeutic agent encapsulated in a coating that comprises the polymer.

Aspect 55. The method of aspect 50, wherein the polymer comprises SIBS.

Aspect 56. The method of aspect 48, wherein the therapeutic agent is a corticosteroid.

Aspect 57. The method of aspect 50, further comprising providing a tie layer over the therapeutic-agent-containing layer.

Aspect 58. The method of aspect 57, wherein the polymeric lead body is a silicone lead body.

Aspect 59. A method of depositing a material on a neurostimulation device lead body comprising an electrical contact, an elongated conductor in electrical communication with the electrical contact and extending along at least a portion of the length of the lead, and a polymeric lead body, said method comprising depositing the material over the lead body without depositing the material over the electrical contacts.

Aspect 60. The method of aspect 59, wherein the material is deposited by a micro-spotting pen.

Aspect 61. The method of aspect 59, wherein the material is deposited by a DNA pen.

Aspect 62. The method of aspect 59, wherein the material is deposited by a maskless mesoscale material deposition.

Aspect 63. The method of aspect 59, wherein the material is deposited by inkjet deposition.

Aspect 64. The method of aspect 59, further comprising the step of placing a mask over the electrical contacts before depositing the material and removing the mask after depositing the material.

Aspect 65. The method of aspect 64, wherein the mask is selected from a polymer mask and semi-conductor masking tape.

Aspect 66. The method of aspect 64, wherein the material is deposited by spray-coating or dip-coating.

Aspect 67. The method of aspect 59, wherein the lead body comprises silicone.

Aspect 68. The method of aspect 59, wherein the material comprises a polymer and a therapeutic agent.

Aspect 69. The method of aspect 68, wherein the polymer comprises SIBS.

Aspect 70. The method of aspect 68, wherein the therapeutic agent comprises dexamethasone.

Aspect 71. A medical device comprising (a) a region comprising silicone, (b) a polymeric layer comprising a first polymer disposed over the region, said first polymer comprising a first monomer and (c) a tie layer between the region and the polymeric layer that comprises a second polymer, said second polymer comprising a silicon-containing monomer, wherein the first and second polymers are different.

Aspect 72. The medical device of aspect 71, wherein the second polymer is a copolymer that comprises a siloxane monomer and said first monomer.

Aspect 73. The medical device of aspect 71, wherein the second polymer is a block copolymer that comprises a polysiloxane block and an additional polymer block.

Aspect 74. The medical device of aspect 73, wherein the additional polymer block comprises said first monomer.

Aspect 75. The medical device of aspect 73, wherein the first polymer is a block copolymer that comprises a polymer block that is the same as the additional polymer block.

Aspect 76. The medical device of aspect 75, wherein the first polymer comprises a polystyrene block and a polyisobutylene block and wherein the additional polymer block is selected from a polystyrene block, a polyisobutylene block or both.

Aspect 77. The medical device of aspect 71, wherein the polymeric layer comprises a therapeutic agent.

Aspect 78. An implantable or insertable medical device comprising (a) a first region comprising silicone, (b) a polymeric layer comprising a first polymer disposed over the first region, said first polymer comprising a first monomer and (c) a tie layer between the first region and the polymeric layer that comprises a second polymer, said second polymer comprising said first monomer, wherein the first and second polymers are different.

Aspect 79. The medical device of aspect 78, wherein the second polymer is grafted to the first region Aspect 80. The medical device of aspect 78, wherein the tie layer is a plasma polymerized tie layer.

Aspect 81. The medical device of aspect 78, wherein the first region comprises an ozonated surface and wherein the tie layer comprises a polymer that is grafted to the ozonated surface.

Aspect 82. The medical device of aspect 78, wherein the second polymer is a block copolymer that comprises a polysiloxane block and an additional polymer block comprising said first monomer.

Aspect 83. The medical device of aspect 78, wherein the polymeric layer comprises a therapeutic agent.

Aspect 84. A medical device comprising (a) a first region comprising silicone, (b) a polymeric layer comprising a first polymer disposed over the silicone, and (c) a tie layer between the first region and the polymeric layer, wherein the tie layer comprises an organosilicon compound.

Aspect 85. The medical device of aspect 84, wherein the organosilicon compound is $SiR^1{}_nR^2{}_{4-n}$ where n is one, two, three or four, where the $R^1$ groups are independently selected from straight chain or branched C1-C10 alkoxy and alkanoyloxy groups, and wherein the $R^2$ groups are independently selected from hydride, anhydride, azide, epoxy, ester, halogen, hydroxyl, isocyanate, phosphate and vinyl groups.

Aspect 86. The medical device of aspect 85, wherein n is one, two or three and wherein the first polymer comprises a functional group that is reactive with the $R^2$ groups.

Aspect 87. The medical device of aspect 86, wherein n is one, two or three and wherein the first polymer comprises an allyl group and wherein the $R^2$ groups comprise at least one hydride group.

Aspect 88. The medical device of aspect 87, wherein the first polymer comprises SIBS.

Aspect 89. The medical device of aspect 86, wherein the organosilicon compound is selected from a dialkloxysilane compound and a trialkloxysilane compound.

Aspect 90. The medical device of aspect 86, wherein the organosilicon compound is selected from triethoxysilane and triacetoxysilane.

Aspect 91. The medical device of aspect 84, wherein the polymeric layer comprises a therapeutic agent.

Aspect 92. A method of improving the adhesion between a first region of a medical device that comprises silicone and a polymeric layer comprising a polymer that this disposed over the first region, said method comprising: swelling the first region with a first solvent; applying a solution comprising the polymer and a second solvent to the swelled silicone, wherein the first solvent and the second solvent may be the same or different; and evaporating the solvent to form the polymeric layer.

Aspect 93. The method of aspect 92, wherein the first and second solvents are the same.

Aspect 94. The method of aspect 92, wherein the polymeric layer comprises a therapeutic agent.

Aspect 95. The method of aspect 92, wherein the polymeric layer comprises a block copolymer.

Aspect 96. The method of aspect 92, wherein the polymeric layer comprises SIBS.

Aspect 97. A method of improving the adhesion between a first region of a medical device that comprises silicone and a polymeric layer comprising a polymer that is disposed over the first region, comprising texturing the surface of the first region to form a textured surface and applying the polymeric layer to the textured surface.

Aspect 98. The method of aspect 97, wherein texturing the surface of the first region comprises mechanically roughening the surface of the first region.

Aspect 99. The method of aspect 97, wherein the textured surface comprises protrusions, depressions, or both.

Aspect 100. The method of aspect 97, wherein the textured surface comprises molded protrusions, molded depressions, or both.

Aspect 101. The method of aspect 97, wherein the textured surface comprises pores.

Aspect 102. The method of aspect 101, wherein the pores are laser ablated pores.

Aspect 103. The method of aspect 101, wherein the pores are molded pores.

Aspect 104. The method of aspect 97, wherein the polymeric layer comprises a therapeutic agent.

Aspect 105. The method of aspect 97, wherein the polymeric layer comprises a block copolymer.

Aspect 106. The method of aspect 97, wherein the polymeric layer comprises SIBS.

Aspect 107. A method of improving the adhesion between a first region of a medical device that comprises partially crosslinked silicone and a polymeric layer comprising a polymer that is disposed over the first region, said method comprising: applying said polymeric layer to said first region and crosslinking the silicone.

Aspect 108. The method of aspect 107, wherein the first region comprises partially crosslinked polydimethylsiloxane.

Aspect 109. The method of aspect 107, wherein the first region comprises polydimethylsiloxane and a crosslinkable polymer other than polydimethylsiloxane, wherein the polymeric layer comprises said crosslinkable polymer other than polydimethylsiloxane, and wherein the first region and the polymeric layer are simultaneously crosslinked.

Aspect 110. The method of aspect 107, wherein the polymeric layer comprises a therapeutic agent.

Aspect 111. The method of aspect 107, wherein the polymeric layer comprises a block copolymer.

Aspect 112. The method of aspect 107, wherein the polymeric layer comprises SIBS.

Although various embodiments are specifically illustrated and described herein, it will be appreciated that modifications and variations of the present invention are covered by the above teachings and are within the purview of the appended claims without departing from the spirit and intended scope of the invention.

The invention claimed is:

1. An implantable or insertable medical device comprising (a) a silicone-containing region that comprises silicone, (b) a polymeric layer comprising a block copolymer and a therapeutic agent disposed over the silicone-containing region, said block copolymer comprising at least one high Tg polymer block comprising at least one first monomer and at least one low Tg polymer block comprising polyisobutylene, and (c) a tie layer between the silicone-containing region and the polymeric layer, said tie layer comprising an additional polymer, wherein the block copolymer and the additional polymer are different from one another, wherein the additional polymer is grafted to the surface of the silicone-containing region, and wherein the additional polymer comprises a monomer selected from styrene, isobutylene, and a combination of styrene and isobutylene.

2. The medical device of claim 1, wherein the at least one high Tg polymer block is a homopolymer or copolymer block comprising at least one first monomer selected from high Tg vinyl aromatic monomers, high Tg alkyl methacrylate monomers, high Tg acrylate monomers, and combinations thereof.

3. The medical device of claim 1, wherein the block copolymer comprises a polystyrene block and a polyisobutylene block.

4. The medical device of claim 1, wherein the block copolymer comprises two polystyrene blocks and a polyisobutylene block between the two polystyrene blocks.

5. The medical device of claim 1, wherein said medical device is a neurostimulation device.

6. The medical device of claim 5, wherein said neurostimulation device is a neurostimulation lead that comprises an electrical contact and an elongated conductor in electrical communication with the electrical contact and extending along at least a portion of the length of the lead, and wherein said silicone-containing region is a polymeric lead body that supports the contact and encapsulates at least a portion of the length of the elongated conductor.

7. The medical device of claim 5, wherein the neurostimulation device is selected from a spinal cord stimulation lead, a deep brain stimulation lead, and a cochlear lead.

8. The medical device of claim 3, wherein the block copolymer further comprises a hydrophilic block.

9. The medical device of claim 8, wherein the hydrophilic block is selected from homopolymer or copolymer blocks comprising monomers selected from carboxylic acid monomers and salts thereof, sulfonic acid monomers and salts thereof, vinyl pyrrolidone, vinyl alcohol, hydroxyethyl methacrylate, methyl methacrylate, hydroxystyrene, methyl vinyl ether, ethylene oxide, and combinations thereof.

10. The medical device of claim 1, wherein the block copolymer is blended with a maleic anhydride polymer.

11. The medical device of claim 10, wherein the maleic anhydride polymer is a styrene-maleic anhydride copolymer and wherein the at least one first monomer of the block copolymer is styrene.

12. The medical device of claim 1, wherein the therapeutic agent is a corticosteroid.

13. The medical device of claim 1, wherein the block copolymer further comprises a polysiloxane block.

14. The medical device of claim 3, wherein said polymeric layer comprises a low molecular weight poly(styrene-b-isobutylene-b-styrene) triblock copolymer, and where said medical device further comprises an additional layer over said polymeric layer that comprises high molecular weight poly(styrene-b-isobutylene-b-styrene) triblock copolymer.

15. The medical device of claim 1, wherein said medical device comprises an antioxidant.

16. The medical device of claim 15, wherein the antioxidant is released into a subject upon implantation into said subject.

17. The medical device of claim 15, wherein the antioxidant is an antioxidant polymer.

18. The medical device of claim 17, wherein the antioxidant polymer is a polymer that comprises a hydroxystyrene monomer.

19. The medical device of claim 1, wherein the additional polymer further comprises a silicon-containing monomer.

20. The medical device of claim 19, wherein the block copolymer comprises a polystyrene block and a polyisobutylene block and wherein the additional polymer is a copolymer that comprises (a) a siloxane monomer and (b) styrene, isobutylene, or a combination of styrene and isobutylene.

21. The medical device of claim 19, wherein the additional polymer is a block copolymer that comprises (a) a polysiloxane block and (b) an additional polymer block comprising said monomer selected from styrene, isobutylene and a combination of styrene and isobutylene.

22. The medical device of claim 19, wherein the block copolymer comprises a polystyrene block and a polyisobutylene block and wherein the additional polymer is a block copolymer comprising (a) a polysiloxane block and (b) a polystyrene block, a polyisobutylene block, or both a polystyrene block and a polyisobutylene block.

23. The medical device of claim 1, wherein the silicone-containing region is ozonated, followed by graft polymerization of the additional polymer.

24. The medical device of claim 1, wherein said silicone-containing region comprises a textured surface comprising protrusions, depressions, or both.

25. The medical device of claim 24, wherein the textured surface comprises laser ablated pores or molded pores.

* * * * *